US010524687B2

(12) United States Patent
Osman

(10) Patent No.: US 10,524,687 B2
(45) Date of Patent: Jan. 7, 2020

(54) RAPID QUANTITATIVE EVALUATIONS OF HEART FUNCTION WITH STRAIN MEASUREMENTS FROM MRI

(71) Applicant: Myocardial Solutions, Inc., Raleigh, NC (US)

(72) Inventor: Nael F. Osman, Cary, NC (US)

(73) Assignee: Myocardial Solutions, Inc., Morrisville, NC (US)

( * ) Notice: Subject to any disclaimer, the term of this patent is extended or adjusted under 35 U.S.C. 154(b) by 351 days.

(21) Appl. No.: 15/498,058

(22) Filed: Apr. 26, 2017

(65) Prior Publication Data

US 2017/0311839 A1 Nov. 2, 2017

Related U.S. Application Data

(60) Provisional application No. 62/415,767, filed on Nov. 1, 2016, provisional application No. 62/328,374, filed on Apr. 27, 2016.

(51) Int. Cl.
*A61B 5/055* (2006.01)
*A61B 5/00* (2006.01)

(52) U.S. Cl.
CPC ............ *A61B 5/055* (2013.01); *A61B 5/0044* (2013.01); *A61B 5/7207* (2013.01);
(Continued)

(58) Field of Classification Search
CPC ....... A61B 5/055; A61B 5/743; A61B 5/0044; A61B 2576/023
See application file for complete search history.

(56) References Cited

U.S. PATENT DOCUMENTS 6,453,187 B1 9/2002 Prince et al.
6,597,935 B2 7/2003 Prince et al.
(Continued)

OTHER PUBLICATIONS

Cerquiera et al., "Standardized Myocardial Segmentation and Nomenclature for Tomographic Imaging of the Heart", Circulation 20023; 105:539-542 (Year: 2002).*
(Continued)

*Primary Examiner* — David C Eastwood
*Assistant Examiner* — Aminah Asghar
(74) *Attorney, Agent, or Firm* — Myers Bigel, P.A.

(57) ABSTRACT

Rapid quantitative evaluations of heart function are carried out with strain measurements from Magnetic Resonance Imaging (MRI) images using a circuit at least partially onboard or in communication with an MRI Scanner and in communication with the at least one display, the circuit including at least one processor that: obtains a plurality of series of MRI images of long and short axis planes of a heart of a patient, with each series of the MRI images is taken over a different single beat of the heart of the patient during an image session that is five minutes or less of active scan time and with the patient in a bore of the MRI Scanner; measures strain of myocardial heart tissue of the heart of the patient based on the plurality of series of MRI images of the heart of the patient; and generates longitudinal and circumferential heart models with a plurality of adjacent compartments, wherein the compartments are color-coded based on the measured strain.

12 Claims, 20 Drawing Sheets
(8 of 20 Drawing Sheet(s) Filed in Color)

(52) U.S. Cl.
CPC ............ *A61B 5/7292* (2013.01); *A61B 5/743* (2013.01); *A61B 2576/023* (2013.01)

(56) References Cited

U.S. PATENT DOCUMENTS

| | | | |
|---|---|---|---|
| 6,892,089 | B1 | 5/2005 | Prince et al. |
| 7,495,438 | B2 | 2/2009 | Prince et al. |
| 7,741,845 | B2 | 6/2010 | Osman |
| 7,800,366 | B1 | 9/2010 | Prince et al. |
| 8,380,281 | B2 | 2/2013 | Osman et al. |
| 8,380,286 | B2 | 2/2013 | Osman et al. |
| 2004/0066958 | A1* | 4/2004 | Chen ................ A61B 6/466 382/128 |
| 2004/0153128 | A1* | 8/2004 | Suresh ............ G06F 19/3481 607/14 |
| 2007/0014452 | A1* | 1/2007 | Suresh ............ G06F 19/3481 382/128 |
| 2007/0016000 | A1* | 1/2007 | Prince ................ A61B 5/055 600/410 |
| 2008/0077032 | A1* | 3/2008 | Holmes ............. A61B 5/055 600/523 |
| 2008/0081997 | A1* | 4/2008 | Kakihara ............ A61B 8/08 600/450 |
| 2009/0281415 | A1 | 11/2009 | Cupps et al. |
| 2010/0123714 | A1 | 5/2010 | Langeland et al. |
| 2010/0215238 | A1* | 8/2010 | Lu .................... G06T 7/12 382/131 |
| 2012/0121152 | A1* | 5/2012 | Lu .................. G06K 9/6282 382/131 |
| 2013/0274592 | A1 | 10/2013 | Shin et al. |
| 2014/0121496 | A1* | 5/2014 | Bi .................... A61B 5/7292 600/413 |
| 2014/0257083 | A1* | 9/2014 | McVeigh ........... A61B 5/0044 600/410 |
| 2014/0347388 | A1 | 11/2014 | Friedman et al. |
| 2015/0077112 | A1* | 3/2015 | Otazo .................. A61B 5/005 324/318 |
| 2015/0133802 | A1* | 5/2015 | Nabutovsky ........ A61B 5/1128 600/508 |
| 2015/0289769 | A1* | 10/2015 | Venkatesh .......... A61B 5/0452 600/410 |
| 2015/0317448 | A1* | 11/2015 | Razavi ................. G16H 50/50 702/19 |
| 2016/0000392 | A1 | 1/2016 | Wong Po Foo et al. |
| 2017/0065242 | A1* | 3/2017 | Chirvasa ............. A61B 5/055 |
| 2017/0337343 | A1* | 11/2017 | Kakadiaris ........... G06F 19/00 |
| 2018/0116725 | A1* | 5/2018 | Ashikaga ........... G09B 23/288 |

OTHER PUBLICATIONS

Yousef et al., "The Effect of Noise on the Accuracy of Strain Measurement when using Strain Encoded (SENC) MRI", Proc. Intl. Soc. Magn. Reson. Med. 14 (2006) (Year: 2006).*

El Harouni, Ahmed "Enhancing Strain-Encoded (SENC) MRI for Breast and Cardiac Imaging" *Dissertation submitted to Johns Hopkins University* (178 pages) (Jan. 2011).

Kitkungvan et al. "Detection of LA and LAA Thrombus by CMR in Patients Referred for Pulmonary Vein Isolation" *JACC: Cardiovascular Imaging* 9(7):809-818 (2016).

Neizel et al. "Strain-Encoded MRI for Evaluation of Left Ventricular Function and Transmurality in Acute Myocardial Infarction" *Circulation: Cardiovascular Imaging* 2(2):116-122 (2009).

Sampath et al. "A combined harmonic phase and strain-encoded pulse sequence for measuring three-dimensional strain" *Magnetic Resonance Imaging* 27(1):55-61 (2009).

International Search Report and the Written Opinion of the International Searching Authority corresponding to International Patent Application No. PCT/US2017/029602 (16 pages) dated Sep. 12, 2017).

* cited by examiner

GLOBAL MEASURES — 130

GLOBAL STRAIN MEASURES

| | RAW | NORMAL |
|---|---|---|
| GLOBAL LONGITUDINAL STRAIN(GLS) | — | (<-17) |
| GLOBAL CIRCUMFERENTIAL STRAIN(GCS) | — | (<-17) |

GLOBAL TRADITIONAL MEASURES

| | RAW | NORMAL |
|---|---|---|
| EF | — | |
| LV MASS | — | |
| LV ES VOLUME | — | |
| LV ED VOLUME | — | |
| LV STROKE VOLUME | — | |

101

REGIONAL SENC STRAIN MEASURES

LONGITUDINAL STRAIN — 110s, 110

| BASAL | | MID | | APICAL | |
|---|---|---|---|---|---|
| 1. ANTERIOR | -9% | 7. ANTERIOR | -21% | 13. ANTERIOR | -19% |
| 2. ANTEROSEPTAL | -8% | 8. ANTEROSEPTAL | -16% | 14. SEPTAL | -22% |
| 3. INFEROSEPTAL | -18% | 9. INFEROSEPTAL | -21% | 15. INFERIOR | -16% |
| 4. INFERIOR | -22% | 10. INFERIOR | -22% | 16. LATERAL | -17% |
| 5. INFEROLATERAL | -16% | 11. INFEROLATERAL | -16% | | |
| 6. ANTEROLATERAL | -23% | 12. ANTEROLATERAL | -23% | | |

RED  YELLOW  DARK GREEN  GREEN  BLUE  PURPLE

| DYSKINETIC | AKINETIC | HYPOKINETIC | KINETIC | HYPER |
|---|---|---|---|---|
| +10% | 0% | -10% | -20% | -30% |

-10%   -17%

101g

CIRCUMFERENTIAL STRAIN

| 3Ch | | 4Ch | | 2Ch | |
|---|---|---|---|---|---|
| BASAL INFEROLATERAL | -13% | BASAL INFEROSEPTUM | -19% | BASAL INFERIOR | -23% |
| MID INFEROLATERAL | -16% | MID INFEROSEPTUM | -22% | MID INFERIOR | -24% |
| APICAL LATERAL | -19% | APICAL SEPTUM | -20% | APICAL INFERIOR | -13% |
| BASAL ANTEROSEPTUM | -6% | BASAL ANTEROLATERAL | -25% | BASAL ANTERIOR | -9% |
| MID ANTEROSEPTUM | -16% | MID ANTEROLATERAL | -22% | MID ANTERIOR | -19% |
| APICAL ANTERIOR | -23% | APICAL LATERAL | -22% | APICAL ANTERIOR | -23% |
| APICAL CAP | -19% | APICAL CAP | -17% | APICAL CAP | -19% |

3Ch — 120s, 120₃
4Ch — 120, 120₄
2Ch — 120, 120₂

| DYSKINETIC | AKINETIC | HYPOKINETIC | KINETIC | HYPER |
|---|---|---|---|---|
| +10% | 0% | -10% | -20% | -30% |

-10%   -17%

© 2016, MYOCARDIAL SOLUTIONS, INC.

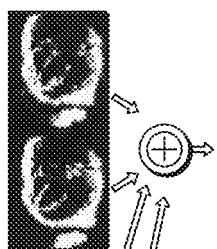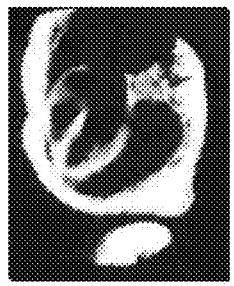

FIG. 9A    FIG. 9B    FIG. 9C    FIG. 9D    FIG. 9E
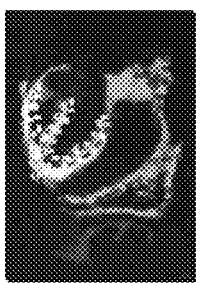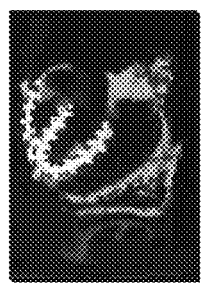
FIG. 9F    FIG. 9G    FIG. 9H
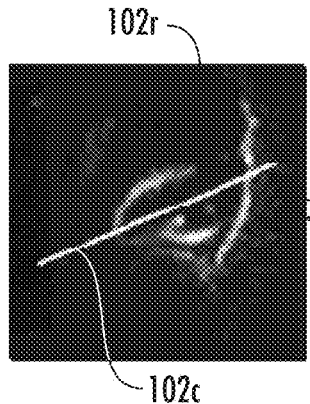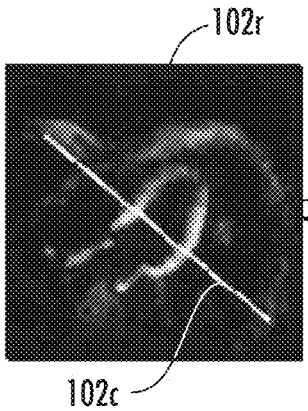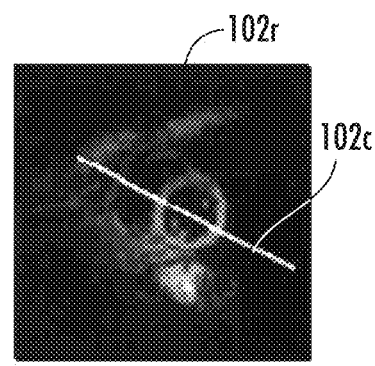
FIG. 10A    FIG. 10B    FIG. 10C

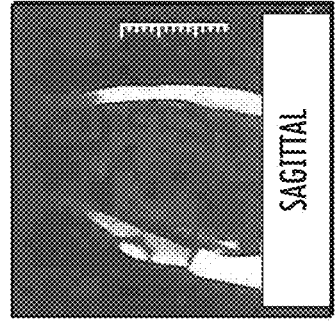
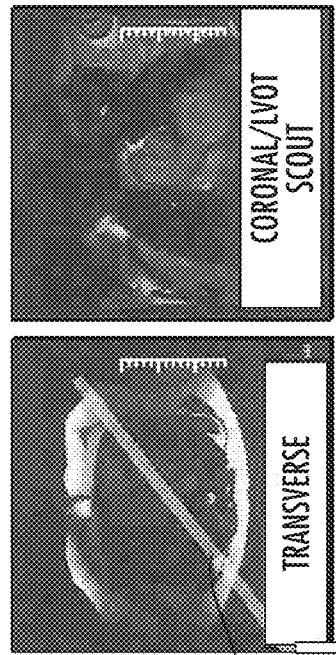
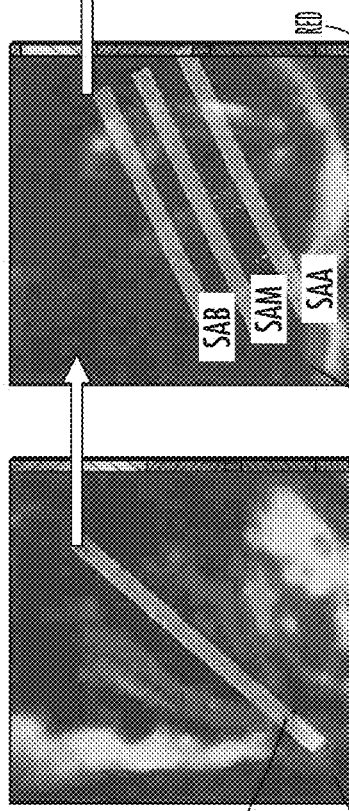
FIG. 11B

RAPID QUANTITATIVE EVALUATIONS OF HEART FUNCTION WITH STRAIN MEASUREMENTS FROM MRI

RELATED APPLICATIONS

This application claims priority to U.S. Provisional Application Ser. No. 62/328,374, filed Apr. 27, 2016, and U.S. Provisional Application Ser. No. 62/415,767, filed Nov. 1, 2016, the contents of which are hereby incorporated by reference as if recited in full herein.

COPYRIGHT NOTICE

A portion of the disclosure of this patent document contains material which is subject to copyright protection. The copyright owner, MyoCardial Solutions, Inc., has no objection to the reproduction by anyone of the patent document or the patent disclosure, as it appears in the Patent and Trademark Office patent file or records, but otherwise reserves all copyright rights whatsoever.

FIELD OF THE INVENTION

The present invention involves the field of Magnetic Resonance Imaging (MRI).

BACKGROUND

Improvements in medical imaging technologies, such as MRI, CT and ultrasound, have made it possible to image internal anatomical features in ways that show both structure and motion. Better diagnosis of certain medical conditions, such as heart disease, generally requires imagery that may be acquired quickly, and that provides information pertaining to both anatomical structure as well as function. Accordingly, there is an ongoing need for quantitative imaging of various tissue regions, such as the heart or other organs, which reduces the subjectivity and dependence on the experience of the reading physician.

Magnetic Resonance Imaging (MRI) has become a leading means of imaging for noninvasive diagnostics. By operating in regions of the electromagnetic spectrum that are benign to tissue, MRI imagery may be acquired repeatedly without danger to the patient. As used herein, the term "imagery" may refer to a single image or multiple images.

Non-MRI medical imaging technologies are generally not well suited for observer-independent imaging. These technologies, such as ultrasound, may involve invasive devices or cutaneous probes that may apply pressure to the patient's body in the vicinity of the tissue being imaged. As such, these imaging technologies may interfere with the function of certain organs by applying pressure, causing tissue deformations that may interfere with the motion and function of the tissue being imaged.

Existing MRI procedures are lengthy (at least 20 minutes) and involve the placement of patients inside the bore of the magnet for at least this duration of time. This has a number of disadvantages. The placement of a patient inside a closed bore magnet, which provides the best quality for imaging the heart, is extremely inconvenient for the patient and is very sensitive to any motion of the patient. Compliance to the restriction of remaining still for extensive periods of time is extremely difficult for patients to maintain; as a result, acquired images of the heart frequently suffer from lower image quality. Also, extensive time inside the magnet is completely troublesome for many patients with different degrees of claustrophobia, which can cause additional motion that interferes with the imaging quality and can cause premature interruption or termination of the imaging, rendering the diagnostic information worthless.

Besides the length of the stay inside the magnet, the acquisition of different images should be carried out with no patient motion, including breathing, during the scan. This requires patients to hold their breath for periods of about 10 seconds and repeat them many times while staying still within the magnet bore.

This complexity of imaging with a need of high compliance of patients reduces significantly the quality of the resulting images of the heart, which results in significant variability between the readers who assess the diagnostic information contained within the images subjectively.

Summary of Embodiments of the Invention

Embodiments of the present invention are directed to systems, circuits and methods for fast, quantitative and comprehensive assessment of the heart by measuring segmental contractility of the wall muscle, noninvasively, optionally also measuring global function. The methods can be carried out rapidly, such as in minimal time for a patient to reside inside the MRI magnet for five minutes or less, typically under five minutes, even as short as 15 seconds, in order to produce all the measurements. The methods produce strain measurements that provide objective assessment of the heart muscle and indication of weakness, and can indicate whether the weakness is reversible or not.

Embodiments of the invention can image the heart at rest or under stress; the latter in case of assessing ischemia resulting from coronary stenosis to evaluate cardiac function or injury or disease, such as to diagnose patients with coronary artery diseases.

Embodiments of the invention are directed to methods, systems and circuits that generate quantitative strain measurements of myocardial deformation that provide objective assessment of heart muscle functionality and indication of weakness, and whether the weakened heart muscle is reversible or not. The methods, systems and circuits can image the heart at rest and/or under stress, the latter assesses ischemia resulting from coronary stenosis to diagnose patients with coronary artery diseases.

Embodiments of the invention provide methods, systems and circuits for fast assessment of heart muscle functionality using MRI with high accuracy and in a short in-bore patient time (typically less than two minutes, such as between 2 minutes and 30 seconds of time spent inside the MRI magnet bore). This period is sufficient to acquire the information needed for calculating strain measurements which can provide a comprehensive assessment of heart muscle functionality.

Embodiments of the invention are directed at rapid, quantitative cardiac evaluations comprising strain based imaging techniques employing Strain Encoded Imaging (SENC), which is an MRI technique for imaging regional deformation of tissue, such as the heart muscle. Producing multiple strain sequences along multiple acquisition planes allows global and/or regional assessment of circumferential and longitudinal strain that correlate to myocardial contraction and function. The present invention involves systems, methods and circuits for fast, quantitative and comprehensive assessment of the heart by measuring global function and segmental contractility of the wall muscle, noninvasively.

The methods, systems and circuits can employ a rapid strain encoding (SENC) pulse sequence to acquire, in a single heartbeat, a sequence of images of heart muscle functionality during the cardiac cycle and within a slice (plane) of the heart. This series of SENC raw images can be combined together to obtain an anatomical sequence and a strain sequence of the heart muscle in that slice. The SENC raw sequence with high tuning shows the tissue of the heart at end-systole as bright in contrast to lung tissue and blood that show darker, typically much darker, than the bright tissue. This contrast allows for fast segmentation of (i.e. isolating in images) the heart muscle to separate from other tissues of the body. The anatomical sequence shows the tissue of the heart as bright as the rest of the tissue of the body while suppressing the signal of the blood inside the heart cavities (known as black blood imaging). The strain sequence shows measurements of the contraction and relaxation of the heart muscle during the cardiac cycle; providing measurements of the contractility of the heart muscle. Further discussion of exemplary SENC pulse sequences and protocols can be found in one or more of U.S. Pat. No. 6,597,935: Method for harmonic phase magnetic resonance imaging; U.S. Pat. No. 7,741,845: Imaging tissue deformation using strain encoded MRI; and U.S. Pat. No. 7,495,438: Three dimensional magnetic resonance motion estimation on a single image plane. The contents of these documents are hereby incorporated by reference as if recited in full herein.

Embodiments of the invention can be carried out with minimal patient time inside the bore of the MRI magnet. The scan sequence can be carried out during free-breathing in under 5 minutes, and for as short as 15-90 seconds, in order to generate the data to produce all the quantitative measurements. For example, the entire scan sequence can be acquired with 6 strain sequences from 6 different planes providing complete assessment of global function and segmental contractility within 6 heartbeats.

The minimum strain (indicating maximum shortening of the muscle associated with peak contraction) provides quantitative assessment of the health of the muscle, whether it is normal or weakened, and whether that weakness is temporary (reversible) or permanent (irreversible). Acquiring a multiplicity of strain sequences for a multiplicity of planes covering the heart calculates global and regional function of the whole heart. For example, 3 short-axis views and 3 long-axis views of the heart can be sufficient for comprehensive understanding of the contractility of the ventricles.

Embodiments of the invention employ strain measurements that provide objective assessment of the heart muscle and indication of weakness, and whether the weakness is reversible or not. Universal strain values indicating whether the myocardium is "normal" and "abnormal", and "reversible and "irreversible" have been validated for male and female genders and all age groups. Strain values less than −17% delineate normal myocardium; strain values between −17% and −10% detect abnormal but reversible myocardium; strain values greater than −10% identify abnormal and irreversible myocardium.

While the embodiments of the invention utilize SENC to measure strain to evaluate contractility of heart muscle during systole, another metric can be used to evaluate the relaxation of heart muscle during diastole. Embodiments of the invention also measure strain rate during the relaxation phase of the heart in the same segments used to calculate strain values. These measurements show a different property of the heart muscle, which is stiffness that can be related to diastolic heart problems. Measuring strain rate during diastole directly measures spatial deformation of the muscle which can be correlated to relaxation. Identifying patients with a minimum diastolic strain rate $<-31$ $sec^{-1}$ identifies patients with myocardial dysfunction who are at risk of diastolic heart failure.

Embodiments of the invention also measure temporal differences in strain and/or strain rate between various chambers of the heart or throughout a single heart chamber to identify dyssynchrony and predict the impact of various management algorithms on the improvement. Evaluating the time difference between peak strain, which is associated with tissue deformation during systole, or calculating previously known and published circumferential uniformity ratio estimate [CURE] index values for patients with left bundle branch block and/or patients with transmural infarcts can be used to determine heart failure that may benefit from resynchronization therapy or other intervention that addresses the delay in myocardial contraction. Measuring strain throughout the cardiac cycle and optimizing predicted ejection fraction improvement by altering the timing of contraction of various chambers and/or throughout the chambers themselves can estimate the likelihood of treatment success utilizing various modalities to identify responders and/or guide the strategy of placement of leads or other stimulation modality to optimize synchrony and contraction of the heart.

Embodiments of the invention include stress exams that can be performed using multiple fast scans of the heart, at least one at rest and at least one in a different degree of stress to detect ischemia characteristic of coronary artery diseases. The stress can be done using stress testing with non-pharmacological or pharmacological stress mechanisms. SENC strain imaging with its higher sensitivity requires less stress to accurately identify ischemic myocardium thus shortening the acquisition time, exposing the patient to far lower levels of stress, and reducing the risks of eliciting a stress response. This may allow identifying ischemia through administration of much smaller doses of pharmacological agents, utilization of less risky agents that evoke a lower stress response, and/or incorporation of non-pharmacological mechanisms such as treadmill, Valsalva maneuvers, minimal exercise of the upper or lower body with the patient in supine position remaining on the table to expedite SENC imaging.

Besides the assessment of the heart, strain imaging can be used for planning for the heart location to prepare for imaging. An important phase of any cardiac MRI is to identify the location of the heart and determine the right orientation of the imaging planes along the heart's primary axes. The radial strain encoding pulse sequence can be used to automate the localization of the heart and determine the imaging planes of the heart. The use of automated planning removes a time-consuming, user-dependent and important part of any cardiac MRI exam. The automated planning may be utilized with SENC imaging of heart functionality or may be incorporated into existing MRI techniques to reduce the time associated with any cardiac MRI exam.

Embodiments of the invention also include automated segmentation of strain sequences to increase the speed of calculating global function and segmental contractility without having to manually create contours that define the heart chamber wall. Automated segmentation can also be utilized during alternative MRI imaging modalities by to increase the speed, reliability, and standardization of segmentation.

Embodiments of the invention that use SENC to segment the heart chambers may also allow rapid and automated calculation of traditional measures (e.g. ejection fraction, chamber volume, stroke volume, chamber mass, etc.) utilizing MRI.

Embodiments of the invention provide SENC imaging to evaluate cardiac function as an addition to, or an alternative to EKG monitoring during cardiac or non-cardiac MRI. By imaging cardiac function periodically with SENC during a particular scan session of a patient, the impact of stressors on the patient, the response of patients to long in-bore times (e.g. claustrophobia, etc.), and/or clinical events that may occur in diseased patients (e.g. myocardial infarction), may be monitored throughout the entire imaging procedure. Thus, embodiments of the invention can provide an automated monitoring system or method that monitors cardiac status or a potential of an adverse event while in the bore of the magnet using SENC imaging and detecting change and generating an alert to a clinician as a safety protocol.

While embodiments of the invention have been optimized for the left and right ventricle, they apply to all chambers of the heart including, besides the left and right ventricles, the left and right atria. These embodiments include SENC imaging of systolic function, diastolic function, and dyssynchrony, although the global strain and strain rate values delineating dysfunctional myocardium may differ for the atria.

Embodiments of the invention include medical decision trees and methods to utilize diagnostic information from standardized SENC strain reports. The applications include guiding medical management to optimize myocardial health, prevent development of heart failure, and/or delay or interrupt heart failure progression. SENC imaging can also be used to predict the impact of treatment to improve myocardial function, identify risk of heart failure progression in patients undergoing or who previously underwent surgical or percutaneous intervention, and identify patients with ischemia indicative of coronary artery disease by comparing strain sequences after evoking a stress response.

Embodiments of the invention are directed to medical workstations that include at least one display and a circuit at least partially onboard or in communication with an MRI Scanner and in communication with the at least one display. The circuit includes at least one processor that: obtains a plurality of series of MRI images of long and short axis planes of a heart of a patient, each series of the MRI images is taken over a different single beat of the heart of the patient during an image session that is five minutes or less of active scan time and with the patient in a bore of the MRI Scanner; measures strain of myocardial heart tissue of the heart of the patient based on the plurality of series of MRI images of the heart of the patient; and generates longitudinal and circumferential heart models with a plurality of adjacent compartments. The compartments are color-coded based on the measured strain.

The circuit with the at least one processor can direct the MRI Scanner to acquire the plurality of series of MRI images as free breathing images without requiring cardiac gating from six different planes of the heart as the long and short axis planes.

The circuit with the at least one processor can generate respective movies of the series of MRI images for the different long and short axis planes and causes the at least one display to display the movies of the MRI images and optionally the myocardial heart tissue in the movies of the MRI images show strain measurements using colors that vary over time based on an amount of strain deformation through the cardiac cycle.

The strain measurements can be color-coded in the heart models to represent five states of heart muscle contractility: hyperkinetic, normokinetic, hypokinetic, akinetic and dyskinetic.

The circuit with the at least one processor can cause the at least one display to concurrently display the plurality of heart models with the strain measurements and can further generate, and cause the at least one display to concurrently display, a visual reference bar that identifies a first universal strain value that corresponds to reversible myocardial dysfunction and a second universal strain value that corresponds to irreversible myocardial dysfunction.

The circuit with the at least one processor can cause the at least one display to concurrently display the generated plurality of heart models with the measured strain, and the generated heart models that can be concurrently displayed can include a three chamber heart model, a four chamber heart model and a two chamber heart model with the measured strain for circumferential strain.

The three chamber heart model, the four chamber heart model and the two chamber heart model can show at least seven adjacent compartments associated with a basal inferolateral compartment, a mid inferolateral compartment, an apical lateral compartment, a basal anteroseptum compartment, a mid anteroseptum compartment, an apical anterior compartment and an apical cap, and each compartment can have a different measured strain value.

The concurrently displayed heart models can include a longitudinal strain compartment model with basal, mid and apical regions. The basal and mid regions can each comprising an anterior compartment, an anteroseptal compartment, an inferoseptal compartment, an inferior compartment, an inferolateral compartment, and an anterolateral compartment. The apical region can include an anterior compartment, a septal compartment, an inferior compartment and a lateral compartment.

The circuit with the at least one processor can direct the MRI Scanner to generate a pulse sequence to obtain the plurality of the series of MRI images of the heart of the patient for measuring the strain with a defined encoding frequency ($w\_0$), a low tuning ($w\_L$) and a high tuning ($w\_H$) as follows:

$$w\_0 = (1+s\_max) \times (1+s\_min)/(s\_max - s\_min) \times 1/H$$

$$w\_L = (1+s\_min)/(s\_max - s\_min) \times 1/H$$

$$w\_H = (1+s\_max)/(s\_max - s\_min) \times 1/H$$

with the condition that $s\_max < 1 + 2 \cdot s\_min$, and where H is the slice thickness in mm.

The circuit with the at least one processor can also obtain a series of MRI images of the heart from transverse, sagittal and coronal planes to generate a pseudo two chamber view of the heart to determine orientation of the heart of the patient in a bore of the MR Scanner; identify a pseudo two-chamber plane or a pseudo four-chamber plane from the obtained MRI images; obtain a series of MRI images from the pseudo two-chamber plane or the pseudo four-chamber plane over a single heart beat; generate a pseudo two-chamber strain encoded movie from the series of MRI images of the pseudo two-chamber plane or generate a pseudo four-chamber strain encoded movie from the series of MRI images of the pseudo four-chamber plane; then identify a pseudo four-chamber plane from the pseudo two chamber strain encoded movie or identifies a pseudo two-chamber plane from the pseudo four chamber strain encoded movie; identify three short axis imaging planes from the pseudo two chamber strain encoded movie as the short axis planes for the plurality of series of the MRI images for the calculated strain measurements; generate short axis basal (SAB), short axis medial (SAM) and short axis apical (SAA) strain encoded movies from the series of MRI images of the three identified short axis planes; and identify three long axis imaging planes from the pseudo two chamber strain encoded movie as the longitudinal planes the plurality of series of MRI images for the strain measurements.

The circuit with the at least one processor can search the series of MRI images from the pseudo two chamber plane and/or the pseudo two chamber strain encoded movie to identify an MRI image with a time with a maximum total intensity signal to identify a close to end systole segment of the cardiac cycle; project a line dividing the left ventricle for the identification of the pseudo 4-chamber plane; and project three lines dividing the left ventricle for the identification of the three short axis plane.

The series of MRI images from the pseudo two chamber plane and/or the pseudo two chamber strain encoded movie can identify the MRI image with the maximum total intensity signal are high tuning raw strain encoded MRI images.

The circuit with the at least one processor can: creates an active shape model (ASM) of a myocardial region of the heart of the patient, with a shape and a plurality of nodes or points; create a myocardial mask by combining two binary masks including a myocardial mask and a blood-pool mask to detect location of the myocardium of the heart of the patient; generate an accumulated (ACC) image which represents the myocardium at end systole; correlate the ACC image with the myocardial mask to determine a location of the myocardium; and track the myocardium through the cardiac cycle using the ASM with the correlation as an initialization for the ASM to obtain the series of MRI images of different long and short axis slices.

The circuit with the at least one processor can calculate diastolic strain rate from the measured strain or as the measured strain using the series of MRI image slices from the long and short axis planes.

The circuit with the at least one processor can also: obtain strain measurements of defined segments of myocardial heart tissue as a function of time as the measured strain; calculate a first derivative of the strain measurements as a function of time; and determine diastolic strain as a maximum positive value of the calculated first derivatives.

The measured strain can include a first set of strain measurements and the generated longitudinal and circumferential heart models can be a first set of the longitudinal and circumferential heart models. The circuit with the at least one processor can also: obtain a second plurality of series of MRI images of long and short axis planes of a heart of a patient after a physical or chemically induced stress challenge, with each series of the MRI images is taken over a different single heartbeat of the heart of the patient during an image session that is five minutes or less of active scan time and with the patient in a bore of the MRI Scanner; and obtain a second set of regional and global strain measurements of the myocardial heart tissue of the heart of the patient based on the second plurality of series of MRI images of the heart of the patient; and generate at least one of: a post-challenge set of the longitudinal and circumferential heart models with the plurality of adjacent compartments, wherein the compartments are color-coded based on the strain measurements from the second series of MRI image slices; or a post-challenge set of the longitudinal and circumferential heart models with the plurality of adjacent compartments, wherein the compartments are color-coded based on a difference between the first and second sets of strain measurements.

The circuit with the at least one processor can generate both of the post-challenge sets of the longitudinal and circumferential heart models and cause the at least one display to concurrently display both of the post-challenge sets with the first set of heart models.

The challenge can be a low stress challenge requiring only an increase in heart rate of 10 beats per minute, and the circuit with the at least one processor can compare the first and second sets of strain measurements based on a low stress challenge the post-challenge The circuit with the at least one processor can evaluate dyssynchrony in heart contraction between chambers of the heart and/or in a single heart chamber of the heart of the patient based on a spatial non-uniformity of strain over a cardiac cycle.

The circuit with the at least one processor can identify dyssynchrony based on a number between 0 to 1, where "0" represents full dyssynchrony and "1" represents full synchrony, calculated for segments and/or chambers of the heart based on a dispersion of peak shortening over time of the cardiac cycle from the strain measurements obtained at different locations of the heart and different points of time of the cardiac cycle.

The circuit can calculate a global strain measurement and compare it to predefined global values shown to designate normal and abnormal tissue to thereby delineate abnormal tissue as reversible or irreversible.

Yet other embodiments are directed to methods of rapidly evaluating cardiac function. The methods include: placing a patient in a bore of an MRI Scanner; electronically obtaining planning views of strain encoded (SENC) MRI images from transverse, sagittal and coronal planes to generate a pseudo two chamber view of the heart to determine orientation of the heart of the patient in a bore of the MR Scanner; identifying a pseudo two-chamber or a pseudo four-chamber imaging plane from the obtained planning views of the SENC images; electronically obtaining a series of MRI images from the pseudo two-chamber imaging plane or the pseudo four-chamber imaging plane over a single heart beat; identifying an MRI image with a maximum total intensity signal as being an MRI image slice associated with end systole (maximum contraction of the heart) from high tuning raw MRI images from the series of MRI images from the pseudo two-chamber or the pseudo four chamber imaging plane over the single heart beat; identifying three short axis imaging planes based on the identified MRI image associated with end systole; identifying three long axis imaging planes from the identified MRI image associated with end systole; obtaining a first series of MRI images for each of the three short axis and the three long axis imaging planes, wherein each of the first series of the MRI images for the three short axis and the three long axis imaging planes are taken over a different single heartbeat of the heart of the patient during an image session, and wherein the planning MRI images and the first series of MRI images of the imaging planes are obtained in under five minutes of active scan time and with the patient in the bore of the MRI Scanner for less than five minutes; generating a first set of regional and global strain measurements of myocardial heart tissue of the heart of the patient based on the obtained first series of MRI images for each of the three short axis and the three long axis imaging planes of the heart of the patient; and generating, within 15 minutes of a patient exiting the bore of the magnet, longitudinal and circumferential heart models with a plurality of adjacent compartments, wherein the compartments are color-coded based on the first set of strain measurements, to thereby rapidly evaluate cardiac function.

The planning views and the obtained first series of MRI imaging views can be free breathing MRI images thereby not requiring breath hold signal acquisition or cardiac gating, and wherein the first series of MRI images are obtained with a patient in the bore of the magnet between 1-3 minutes.

The method can also include: presenting a stress-challenge to the patient; obtaining a second series of MRI images for each of the three short axis and the three long axis imaging planes, wherein each of the second series of the MRI images for the three short axis and the three long axis imaging planes are taken over a cardiac cycle of a different single heartbeat of the heart of the patient during an image session that is under five minutes of active scan time and with the patient in the bore of the MRI Scanner; generating a second set of regional and global strain measurements of myocardial heart tissue of the heart of the patient based on the obtained second series of MRI images for each of the three short axis and the three long axis imaging planes of the heart of the patient; and generating, within 15 minutes of a patient exiting the bore of the magnet, longitudinal and circumferential heart models with a plurality of adjacent compartments, wherein the compartments are color-coded based on the second set of strain measurements.

The method can also include generating a post-challenge set of the longitudinal and circumferential heart models with the plurality of adjacent compartments, and the compartments can be color-coded based on a difference between the first and second sets of strain measurements.

The method can include concurrently displaying the heart models with the first and second set of strain measurements and a post-challenge set of heart models based on a change in strain values of the different compartments of the heart models.

The stress challenge can be a low stress challenge requiring only an increase in heart rate of 10 beats per minute.

The method can include electronically valuating dyssynchrony in heart contraction between chambers of the heart and/or in a single heart chamber of the heart of the patient based on a spatial non-uniformity of strain over a cardiac cycle.

The method can include electronically calculating dyssynchrony for all segments of the heart models over a time cycle of the cardiac cycle based on a dispersion of peak shortening over time of the cardiac cycle from the first set of strain measurements obtained at different locations of the heart and different points of time of the cardiac cycle.

Other embodiments are directed to methods of monitoring a heart of a patient during an MRI scanning session. The methods include: electronically obtaining a series of MRI images of target anatomy of a patient during an MRI scan session over a single heart beat; electronically obtaining a series of strain encoded (SENC) MRI images of a heart of the patient during the MRI scan session; electronically automatically monitoring status of the heart of the patient during the scan session to detect a potential adverse heart event during the scan session based on the obtained SENC MRI images; and electronically automatically generating an alert if a potential adverse heart event is detected.

Yet other embodiments are directed to methods of identifying cardiac dysfunction or injury. The methods include: (electronically) comparing strain measurements of different chambers of the heart or different regions of the heart to identify dyssynchrony based on a spatial non-uniformity of strain over a cardiac cycle.

Other embodiments are directed to method s of evaluating cardiac status by electronically determining diastolic strain measurements of the heart of the patient using strain encoded (SENC) MRI images of MRI image slices from long and short axis planes to evaluate at least one of cardiac function, impairment, disease or injury.

Yet other embodiments are directed to a workstation that includes: at least one display; and a circuit at least partially onboard or in communication with an MRI Scanner and in communication with the at least one display. The circuit includes at least one processor that: obtains a plurality of series of MRI images of long and short axis planes of a heart of a patient, wherein each series of the MRI images is taken over a different single heartbeat of the heart of the patient during an image session that is under five minutes of active scan time and with the patient in a bore of the MRI Scanner; and obtains systolic and diastolic strain measurements of the heart of the patient using the series of MRI images from the long and short axis planes. The systolic strain measurements are negative and the diastolic strain measurements are positive, optionally the diastolic strain measurements include calculating a first derivative of strain as a function of time.

The circuit with the at least one processor can obtain strain measurements of defined segments of myocardial heart tissue as a function of time; calculate a first derivative of the strain measurements as a function of time; and determine diastolic strain as a maximum positive value of the calculated first derivatives.

Yet other embodiments are directed to methods of planning scan planes of a heart of a patient. The methods include: electronically obtaining strain encoded MRI images from transverse, sagittal and coronal planes to generate a pseudo two chamber view of the heart to determine orientation of the heart of the patient in a bore of the MR Scanner; electronically identifying a pseudo two-chamber plane or a pseudo four-chamber plane from the obtained MRI images; electronically obtaining a series of MRI images from the pseudo two-chamber plane or the pseudo four-chamber plane over a single heart beat; electronically reviewing the obtained series of MRI images to identify an MRI image with a time with a maximum total intensity signal representing an end systole segment of the cardiac cycle; projecting three lines dividing the left ventricle of the identified MRI image to identify three short axis imaging planes; and projecting dividing lines through the identified MRI image to identify three long axis imaging planes.

The series of MRI images can e from the pseudo two-chamber plane and/or a pseudo two-chamber strain encoded movie generated from the series of MRI images from the pseudo two-chamber plane used to identify the MRI image slice with the maximum total intensity signal are high tuning raw strain encoded movies.

The series of MRI images can be from the pseudo four-chamber plane and/or a pseudo four-chamber strain encoded movie generated from the series of MRI images from the pseudo four-chamber plane used to identify the MRI image slice with the maximum total intensity signal are high tuning raw strain encoded movies.

Still other embodiments are directed to methods for rapid MRI imaging of the heart. The methods include: electronically providing a SENC pulse sequence from a single view of a cut of the heart to acquire a strain movie, and then acquiring a multiplicity of movies from a multiplicity of views of cuts of the heart. Each movie is acquired in a single heartbeat.

Yet other embodiments are directed to methods for quantifying muscle contractility from MRI images that include: electronically transmitting a multiplicity of SENC pulse sequences; electronically acquiring strain movies from the SENC pulse sequences of multiple views of the heart; electronically calculating strain measurement values at individual segments of heart muscle from the strain movies; and color coding the strain values in at least one model of the heart based on a degree of contractility associated with the calculated strain measurement values.

Additional embodiments are directed to methods for quantifying stress on muscle contractility of a heart of a patient from MRI images. The methods include: transmitting a multiplicity of SENC pulse sequences from multiple views of the heart; acquiring strain movies from the SENC pulse sequences of the multiple views of the heart; electronically automatically calculating strain values at individual segments of heart muscle from the strain movies; and color coding a reduction in contractility in compartments of at least one heart model upon application of a stress to the patient to indicate reduced blood perfusion associated with coronary artery disease.

Yet other embodiments are directed to MRI systems that include a processor that uses SENC images (raw and/or colored) for automatically planning of an imaging view to thereby provide a suitable imaging view without requiring human identification of a suitable imaging view based on multiple long and short axis planning views for the imaging view.

Still other embodiments are directed to MRI systems with at least one processor that automatically carries out a segmentation of heart ventricles of a patient from SENC images (raw and/or colored) and measures dimensions of the heart ventricles of the patient from the SENC images.

Yet other embodiments are directed to imaging processing systems for MRI systems with a circuit that generates a series of SENC raw heart images that are combined together to obtain an anatomical sequence and a strain sequence of heart muscle, with the strain sequence of heart images having color-coded perimeters or segments corresponding to calculations of strain values. The strain values include at least one of strain rate, mean strain or average strain.

BRIEF DESCRIPTION OF DRAWINGS

The patent or application file contains at least one drawing executed in color. Copies of this patent or patent application publication with color drawings will be provided by the Office upon request and payment of the necessary fee.

FIG. 5A illustrates the cardiac strain standardized models prior to applying patient strain data. FIG. 5B illustrates the patient inserted into the magnet bore to allow acquisition of strain sequences. FIG. 5C illustrates the cardiac evaluation module scanning the heart for a plurality of different views (shown as six slices) and producing a movie of the moving heart for each in rapid fashion (i.e., under 1 minute). FIG. 5D illustrates contouring a strain sequence along one plane so the cardiac module can calculate global and segmental strain values in order to generate a report while the patient is extracted from the magnet. FIG. 5E illustrates another contour generated from a different strain sequence along a different plane and the display with a report with the raw (pre or no stress) data of global and segmental strain values, and an adjacent window with cardiac images.

FIG. 6 is an exemplary outcome report with global measurements and short and long axis compartmental models with populated with calculated strain values and may optionally include global and other measurements according to embodiments of the present invention.

FIGS. 9A-9H illustrate a sequence of actions to construct an ACC ("Accumulate") image according to embodiments of the present invention.

FIGS. 10A-10C are SENC raw images with cuts/slice planes that can be used for fast automated planning for imaging views according to embodiments of the present invention.

FIG. 11B shows a graphic illustration of a series of actions and outputs including the produced images of the fast planning steps described by FIG. 11A according to embodiments of the present invention.

DETAILED DESCRIPTION

Figure 1:
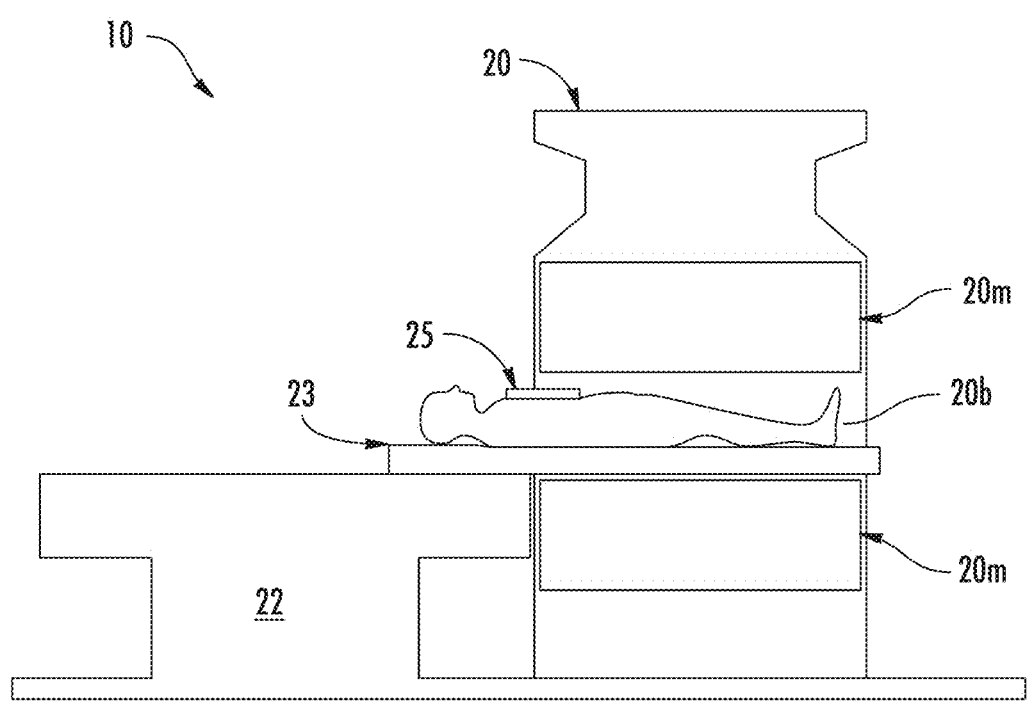
FIG. 1 is a schematic of an exemplary MRI Scanner system.

The present invention now will be described more fully hereinafter with reference to the accompanying drawings, in which illustrative embodiments of the invention are shown. Like numbers refer to like elements and different embodiments of like elements can be designated using a different number of superscript indicator apostrophes (e.g., 10, 10', 10", 10'''). The terms "Fig." and "FIG." may be used interchangeably with the word "Figure" as abbreviations thereof in the specification and drawings. In the figures, certain layers, components or features may be exaggerated for clarity, and broken lines illustrate optional features or operations unless specified otherwise.

In the drawings, the relative sizes of regions or features may be exaggerated for clarity. This invention may, however, be embodied in many different forms and should not be construed as limited to the embodiments set forth herein; rather, these embodiments are provided so that this disclosure will be thorough and complete, and will fully convey the scope of the invention to those skilled in the art.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

Spatially relative terms, such as "beneath", "below", "lower", "above", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below.

The term "about" refers to numbers in a range of +/−20% of the noted value.

As used herein, the singular forms "a", "an" and "the" are intended to include the plural forms as well, unless expressly stated otherwise. It will be further understood that the terms "includes," "comprises," "including" and/or "comprising," when used in this specification, specify the presence of stated features, integers, steps, operations, elements, and/or components, but do not preclude the presence or addition of one or more other features, integers, steps, operations, elements, components, and/or groups thereof. It will be understood that when an element is referred to as being "connected" or "coupled" to another element, it can be directly connected or coupled to the other element or intervening elements may be present. As used herein, the term "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of this specification and the relevant art and will not be interpreted in an idealized or overly formal sense unless expressly so defined herein.

Embodiments of the invention are intended to improve the ability of MRI imaging to more quickly quantify and/or provide standardized reports that identify heart abnormalities and trends for physicians to direct patient management and/or treatment.

The term "circuit" refers to an entirely software embodiment or an embodiment combining software and hardware aspects, features and/or components (including, for example, a processor and software associated therewith embedded therein and/or executable by, for programmatically directing and/or performing certain described actions, operations or method steps).

The term "programmatically" means that the operation or step can be directed and/or carried out by a digital signal processor and/or computer program code. Similarly, the term "electronically" means that the step or operation can be carried out in an automated manner using electronic components rather than manually or using any mental steps.

The terms "MRI scanner" and MR scanner" are used interchangeably to refer to a Magnetic Resonance Imaging system and includes the high-field magnet and the operating components, e.g., the RF amplifier, gradient amplifiers and processors that typically direct the pulse sequences and select the scan planes. Examples of current commercial scanners include: GE Healthcare: Signa 1.5 T/3.0 T; Philips Medical Systems: Achieva 1.5 T/3.0 T; Integra 1.5 T; Siemens: MAGNETOM Avanto; MAGNETOM Espree; MAGNETOM Symphony; MAGNETOM Trio; and MAGNETOM Verio. It is contemplated that both vertical and horizontal bore MRI scanner systems may be used.

As is well known, the MR scanner can include a main operating/control system that is housed in one or more cabinets that reside in an MR control room while the MRI magnet resides in the MR scan suite. The control room and scan room can be referred to as an MR suite and the two rooms can be separated by an RF shield wall. The term "high-magnetic field" refers to field strengths above 0.5 T, typically above 1.0 T, and more typically between about 1.5 T and 10 T. Embodiments of the invention may be particularly suitable for 1.5 T and 3.0 T systems, or higher field systems such as future contemplated systems at 4.0 T, 5.0 T, 6.0 T, 7 T, 8 T, 9 T and the like. Embodiments of the invention may also be useful with lower field portable MRI scanner systems.

The methods and systems can also be applied to animal MRI data acquired from animal MRI scanners but may be particularly suitable for human patients.

The term "patient" refers to humans and animals. Embodiments of the invention may be particularly suitable for human patients.

The term "automatically" means that the operation can be substantially, and typically entirely, carried out without manual input, and is typically programmatically directed and/or carried out. The term "electronically" with respect to connections includes both wireless and wired connections between components.

The term "clinician" means physician, radiologist, cardiologist, physicist, technician, nurse, physician assistant, or other medical personnel desiring to review medical data of a patient.

The term "workstation" refers to a display and/or computer associated with an MR scanner. The workstation and/or computer or circuit with at least one processor can communicate the MR scanner, can be partially or totally onboard the MR scanner and can be remote from the MR scanner, for access by a clinician.

Embodiments of the present invention may take the form of an entirely software embodiment or an embodiment combining software and hardware, all generally referred to herein as a "circuit" or "module." Furthermore, the present invention may take the form of a computer program product on a computer-usable storage medium having computer-usable program code embodied in the medium. Any suitable computer readable medium may be utilized including hard disks, CD-ROMs, optical storage devices, a transmission media such as those supporting the Internet or an intranet, or magnetic storage devices. Some circuits, modules or routines may be written in assembly language or even microcode to enhance performance and/or memory usage. It will be further appreciated that the functionality of any or all of the program modules may also be implemented using discrete hardware components, one or more application specific integrated circuits (ASICs), or a programmed digital signal processor or microcontroller. Embodiments of the present invention are not limited to a particular programming language.

Computer program code for carrying out operations of the present invention may be written in an object oriented programming language such as Java®, Smalltalk or C++. However, the computer program code for carrying out operations of the present invention may also be written in conventional procedural programming languages, such as the "C" programming language. The program code may execute entirely on the user's computer, partly on the user's computer, as a stand-alone software package, partly on the user's computer and partly on another computer, local and/or remote or entirely on the other local or remote computer. In the latter scenario, the other local or remote computer may be connected to the user's computer through a local area network (LAN) or a wide area network (WAN), or the connection may be made to an external computer (for example, through the Internet using an Internet Service Provider).

Embodiments of the invention may be carried out using a cloud computing service (or an aggregation of multiple cloud resources), generally referred to as the "Cloud". Cloud storage may include a model of networked computer data storage where data is stored on multiple virtual servers, rather than being hosted on one or more dedicated servers. Firewalls and suitable security protocols can be followed to exchange and/or analyze patient data.

Strain imaging techniques that have improved upon traditional MRI techniques include Strain Encoded imaging (SENC), which is an MRI technique for imaging regional deformation of tissue, such as the heart muscle. Prior, related art developments in MRI are not capable of providing high quality imagery of tissue that includes a quantitative measure of tissue deformation. SENC is able to measure movement of the heart muscle itself without relying on calculation of changes between the epicardium and endocardium to estimate regional wall motion. Directly measuring myocardial wall motion with SENC eliminates errors derived from manual estimation that hinder prior MRI or Non-MRI techniques of evaluating heart functionality.

The MRI Imaging System Incorporating SENC

The MRI system 10 (FIG. 1) uses an MRI scanner 20 with a high-magnetic field magnet 20m (1.5 T, 3 T or even greater or lower magnetic field strength), where the patient can be positioned on top of a translatable MRI table top 23 held by a table 22. The table top 23 can move and slide into and out of the MRI magnet bore 20b. This motion can be controlled from inside the MRI magnet room or from the console outside the magnet room (in the control room of an MRI suite, for example). Specialized or conventional chest coils 25 for imaging the thorax or the heart can be used. Although the patient can be in any position for imaging, a representative position for heart patients is to lie on their backs and enter the MRI feet first. It is also noted that vertical bore systems may also be used.

Figure 2A:
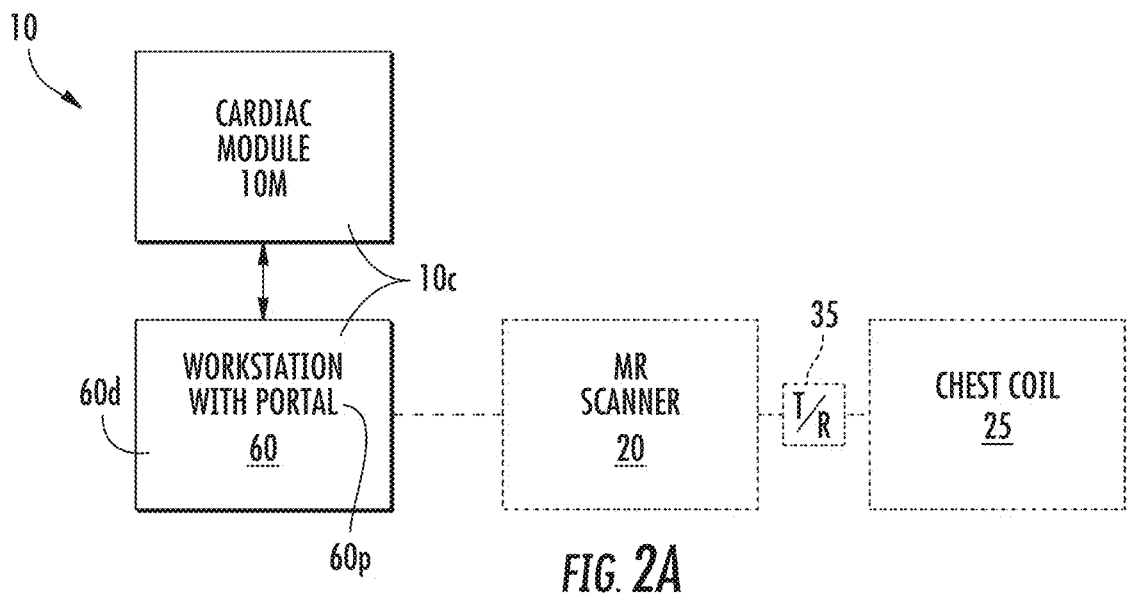
FIGS. 2A-2C are schematic illustrations of different configurations of MRI imaging systems according to embodiments of the present invention.
Figure 2B:
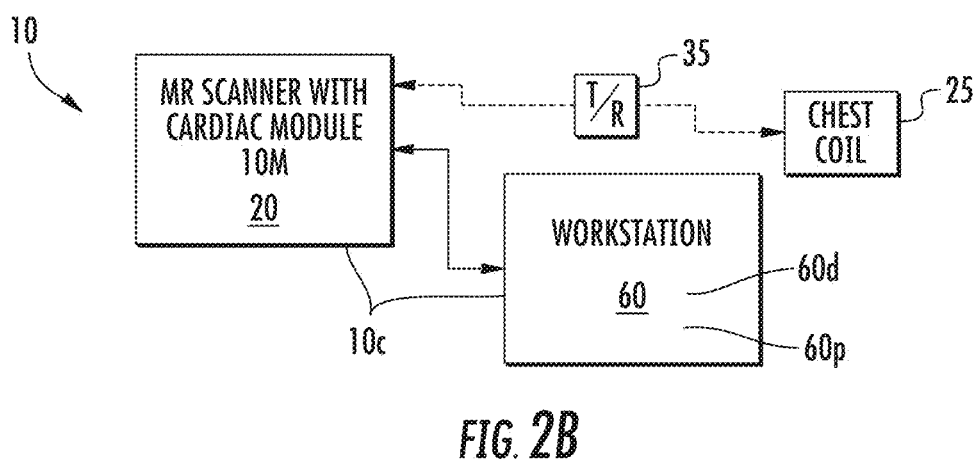
Figure 2C:
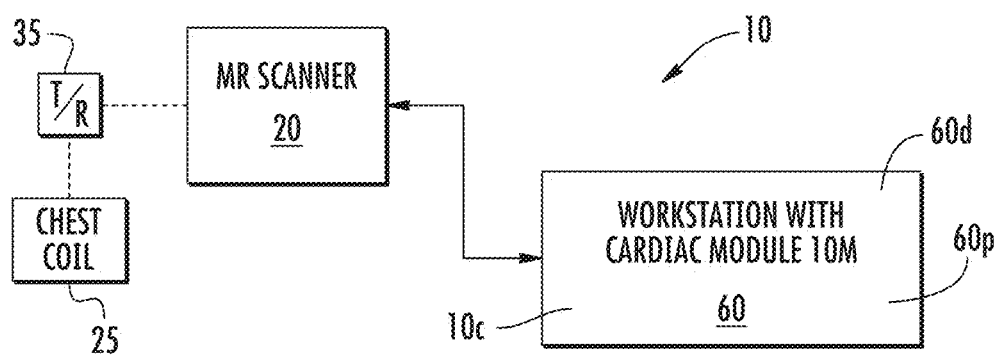

FIGS. 2A-2C are schematic illustrations of different configurations of the MRI imaging system 10 according to embodiments of the present invention. The MRI imaging system incorporates an MR Scanner 20 with a high-magnetic field magnet 20m having a bore 20b, and includes the SENC pulse sequence and a workstation 60. The workstation 60 communicates with a cardiac module 10M and the module 10M can contain the software to generate the SENC pulse sequence and create strain sequences and compile the outcomes into standardized reports and/or heart models of global and regional values of circumferential and longitudinal strain that correlate to myocardial contraction and function. The workstation 60 can include a display 60d. The system 10 can include a circuit 10c with at least one processor for imaging processing the obtained MRI images and/or can comprise one or both of an SENC pulse sequence and/or the strain sequences and calculations that is onboard or remote from the workstation and comprises the module 10M. The system 10 can include a T/R switch 35 that can communicate with a chest coil 25.

FIG. 2A illustrates that the system 10 can include at least one workstation 60 that has a portal for accessing the circuit 10c and/or cardiac module 10M. The circuit 10c may include at least one processor configured to provide the SENC pulse sequences, analyze the raw SENC images and/or calculate the strain measurements. The module 10M can be held on a remote server accessible via a LAN, WAN or Internet. The workstation 60 can communicate with the MR Scanner 20 and chest coil 25. The MR Scanner 20 typically directs the operation of the pulse sequence and image acquisition using the chest coil 25 and at least on transmit/receive switch 35 as is well known to those of skill in the art. The chest coil 25 can be any suitable thoracic or chest coil. The workstation 60 can include a display 60d with a GUI (graphic user input) and the access portal 60p. The workstation 60 can access the module 10M via a relatively broadband high speed connection using, for example, a LAN or may be remote and/or may have lesser bandwidth and/or speed, and for example, may access the data sets via a WAN and/or the Internet. Firewalls may be provided as appropriate for security.

FIG. 2B illustrates that the module 10M can be partially or totally included in the MR Scanner 20 (i.e., a control console or computer) which can communicate with a workstation 60. The module 10M can be integrated into the control cabinet of the MR Scanner with image processing circuitry. The workstation 60 can be in the magnet room and/or the control room of an MRI suite or may be remote from the MRI suite.

FIG. 2C illustrates that the module 10M can be integrated into one or more local or remote workstations 60 that communicates with the MR Scanner 20. Although not shown, parts of the module 10M can be held on both the Scanner 20 and one or more workstations 60, which can be remote or local.

Some, or all, of the cardiac module 10M can be held on at least one server that can communicate with one or more Scanners 20. The at least one server can be provided using cloud computing which includes the provision of computational resources on demand via a computer network. The resources can be embodied as various infrastructure services (e.g., compute, storage, etc.) as well as applications, databases, file services, email, etc. In the traditional model of computing, both data and software are typically fully contained on the user's computer; in cloud computing, the user's computer may contain little software or data (perhaps an operating system and/or web browser), and may serve as little more than a display terminal for processes occurring on a network of external computers. Firewalls and suitable security protocols can be followed to exchange and/or analyze patient data.

Single Heartbeat SENC Acquisition

Strain Encoded Imaging (SENC) is an MRI technique for imaging regional deformation of tissue, such as the heart muscle. The embodiments of the invention use a SENC pulse sequence to acquire a movie (a series of successive MRI images) of strain during a single heartbeat in a single view of a respective cut/slice of the heart using MRI. Multiple strain sequences are then acquired from predefined cuts (the word "cuts" is also referred to interchangeably herein as "slices" or "planes") of the heart to quantify global and regional values of circumferential and longitudinal strain that correlate to myocardial contraction and function.

Setting the SENC Pulse Sequence

In a representative embodiment, the following mathematical equations/formulas can be used to set the parameters of the SENC pulse sequence to measure the contraction of the heart muscle:

"Low- and High-Tuning" Raw SENC images. Raw SENC images are the images produced by the SENC pulse sequence. The raw images are used to estimate the strain from changes in intensity because of contraction. To do so, two different kinds of raw SENC images can be produced: one to capture the contraction of muscle, called "high tuning", and the other to capture the no contraction or even stretching of the muscle, and this is called the "low tuning" images.

Formulas for designing the pulse sequence to measure strains inside the heart measure the strain within a range between maximum strain (s_max) and minimum strain (s_min), define the encoding frequency (w_0) and the low tuning (w_L) and high tuning (w_H) as follows:

$$w\_0 = (1+s\_max) \times (1+s\_min)/(s\_max-s\_min) \times 1/H$$

$$w\_L = (1+s\_min)/(s\_max-s\_min) \times 1/H$$

$$w\_H = (1+s\_max)/(s\_max-s\_min) \times 1/H$$

with the condition that
s_max<1+2.s_min,
where H is the slice thickness in mm.

For example, to image the strain inside the heart myocardium with a maximum contraction of 30%, which is the upper bound of healthy heart contraction (and can't be exceeded), then s_min=−0.30. The negative sign indicates contraction (shortening) of the muscle.

In this example, the maximum range of the strain is:

$$s\_max < 1 + 2 \times s\_min \text{ (i.e. } s\_max < 0.40\text{)}$$

which means that the maximum strain that can be measured is 40% stretching.

Assuming the slice thickness is 10 mm. Then, $$w\_0 = (1+0.4) \times (1-0.3)/(0.4-(-0.3)) \times 1/10 = 0.14 \text{ mm}^{-1}$$

$$w\_L = (1-0.3)/(0.4-(-0.3)) \times 1/10 = 0.10 \text{ mm}^{-1}$$

$$w\_H = (1+0.4)/(0.4-(-0.3)) \times 1/10 = 0.2 \text{ mm}^{-1}$$

By setting the pulse sequence parameters as described above, the imaging sequence will measure strain accurately between +40% and −30%. The slice thickness can be the same or different between different slices, but is preferably the same. The slice thickness can be any appropriate thickness and is typically between 1 mm and 10 mm, more typically between 5-10 mm.

For additional discussion of SENC imaging, see, Neizel et al., Strain-Encoded MRI for Evaluation of Left Ventricular Function and Transmurality in Acute Myocardial Infarction, Circ. Cardiovasc Imaging, 2009: 2: 116-122; and Sampath et al., A combined harmonic phase and strain-encoded pulse sequence for measuring three dimensional strain, Magn Reson Imaging, 2009; 27(1): 55-61, the contents of which are hereby incorporated by reference as if recited in full herein.

Fast Scanning Using SENC Imaging

The methods, systems and circuits of the invention employ a rapid strain encoding (SENC) pulse sequence to acquire, in a single heartbeat, a sequence of images of heart muscle functionality during the cardiac cycle and within a slice (plane) of the heart. This series of SENC raw images are combined together to obtain an anatomical sequence and a strain sequence of the heart muscle in that slice. The anatomical sequence shows the tissue of the heart as bright in contrast to lung tissue and blood that show much darker. This contrast allows for fast segmentation of (i.e. isolating in images) the heart muscle to separate from other tissues of the body. The strain sequence shows measurements of the contraction and relaxation of the heart muscle during the cardiac cycle; providing measurements of the contractility of the heart muscle.

The anatomical and strain sequences also allow quick and repeatable calculations of global measures such as ejection fraction. SENC imaging techniques that enable fast segmentation of the heart chambers also enable rapid and automated calculation of traditional measures (e.g. ejection fraction of heart chambers, chamber volume, stroke volume, chamber mass, etc.). The ability to quickly evaluate traditional measures with higher resolution images, characteristic of MRI, provides standardized metrics that can augment strain mapping to provide the clinician with critical information from which to diagnose and treat patients at risk of developing new or worsening heart failure.

Embodiments of the invention can be carried out with minimal patient time inside the bore of the MRI magnet. The scan sequence can be carried out during free-breathing and for as short as 5 minutes, more typically between 2 minutes and 15 seconds or less in order to generate the data to produce all the quantitative measurements. For example, the entire scan sequence can be acquired with as few as 4-6 strain sequences from 4-6 different imaging planes providing complete assessment of global function and segmental contractility within 4-6 heartbeats. The fast scan thereby produces a multiplicity of movies from a multiplicity of views or cuts of the heart where each movie is acquired in as fast as a single heartbeat. The term "movie" refers to a time sequence of a series of MRI images taken over a cardiac cycle and may be "raw" or unenhanced or may be color-coded with strain measurements, for example.

The advantages to Fast Scanning using SENC imaging include:

Minimal Time Inside the Magnet for Scan Sequence Acquisition
  A minimal amount of time the patient needs to remain inside the bore of the magnet to complete the fast scan and the acquisition of the multiplicity of movies from which the strain sequences are obtained.
  Since the number of strain sequences is determined by the number of planes and each strain sequence can be acquired in a single heartbeat, the duration of time inside the magnet is dependent on the number of planes which correlates to the number of heartbeats.

No Breath Hold Required
  The fast scan can be performed while the subject is freely breathing, without requiring several breath-holds as required by traditional methods.
  Since no segmental acquisition or signal averaging between image sets is required and each strain sequence can be acquired in one heartbeat, the patient can continue to breathe throughout the scanning procedure.

Fast Planning for Imaging Views
  The fast planning can be used to prepare for the fast scan by delineating the position of the heart and defining the principal axes of the heart.
  The preparation for any cardiac acquisition, not limited to the fast planning acquisition, can be done using the single heartbeat SENC acquisition.
  The raw images of the strain sequence, acquired from one heartbeat movie, can be used in its raw form for fast planning.
  The strain sequence images of the one heartbeat movie acquisition can be color-coded based on the recorded levels of strain to be used for fast planning.

Color (Coded) Strain Movies
  The strain images of the different one heartbeat movie acquisitions can each be serially or concurrently presented in color-coded form on the display at the workstation with the Rapid Strain-based Cardiac Evaluation module/circuit.
  The color-coded strain movies can show (instantaneous) strain values that vary in color based on the amount of deformation quantified throughout the cardiac cycle.

Strain Mapping
  Objective Muscle Contractility State: Strain values are used to indicate conventional states of muscle contractility, including Hyperkinetic, Normokinetic, Hypokinetic, Akinetic, and Dyskinetic.
  Color-coding of Contractility State: A coloring scale can be used/provided to visually identify the contractility states of the muscle.
  Strain for Screening: Deviation in the strain values of a heart muscle is indicative of progressive heart disease. Heart failure and/or weakened myocardial function can be caused by different diseases, including, for example, cardiotoxicity, kidney diseases, hypertension, diabetes, viral infections, myocardial infarction, and coronary artery disease.

Standardized Strain Calculations
  Normal Contraction Cut Off: A pre-defined cutoff strain value (e.g. −17%) identifies/detects abnormal contractility. Myocardium with systolic strain values <−17% at systole identifies normal contractility.
  Reversibility of Myocardial Injury Cut Off: A pre-defined low cutoff strain value (−10%) indicates weak muscle contractility that delineates irreversibly from reversibly damaged myocardium. Myocardial contractility with systolic strain values >−10% identifies irreversibly damaged myocardium.
  Myocardial contractility with systolic strain values between the −17% abnormal contractility cutoff and the −10% irreversibly damaged cutoff identifies abnormal but reversibly damaged myocardium.
  The ability to quantify the amount and degree of myocardial injury is able to guide therapeutic or palliative management regimens.
  Continued monitoring of the extent of myocardial injury can evaluate the progressive remodeling that occurs and impact of treatment modalities.
  The "normal" versus "abnormal" cutoff strain value and the "reversible" versus "non-reversible" damage strain cutoff value can be "universal" meaning that the same cut off values are clinically valid across gender and different age groups from pediatric to geriatric, for systolic strain.

The Fast Scan Acquisition

Prior to acquiring the fast scans, planning including patient positioning and planes definition are performed. This can be done in the conventional way as in traditional CMR or can be automated, as will be described later. The imaging planes can include at least 3 short axis planes covering the base, mid and apex of the ventricles. The imaging planes can also include at least one long axis plane (4-chamber view showing all the compartments of the heart) for a minimum of 4 planes. A representative case defines 3 long-axis views, adding 2-chamber and 3-chamber views to the 4-chamber view for a total of 6 planes. The imaging planes can be identified in a very fast way if the fast strain encoded imaging is used with its single heartbeat acquisition for each sequence of images on a single plane.

Figure 3A:
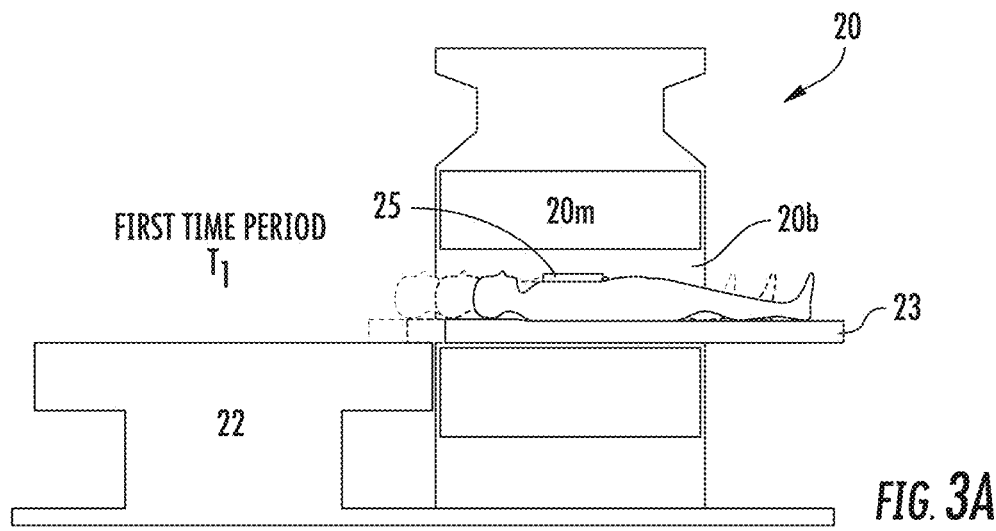
FIGS. 3A-3C are schematic illustrations of an example of a series of steps for obtaining cardiac image signal with minimal duration time in a bore of a magnet according to embodiments of the present invention.
Figure 3B:
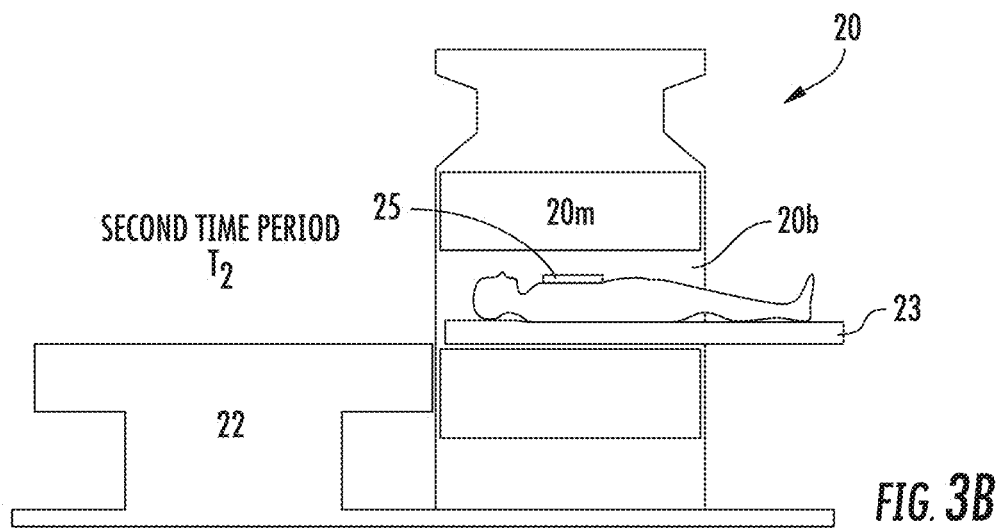
Figure 3C:
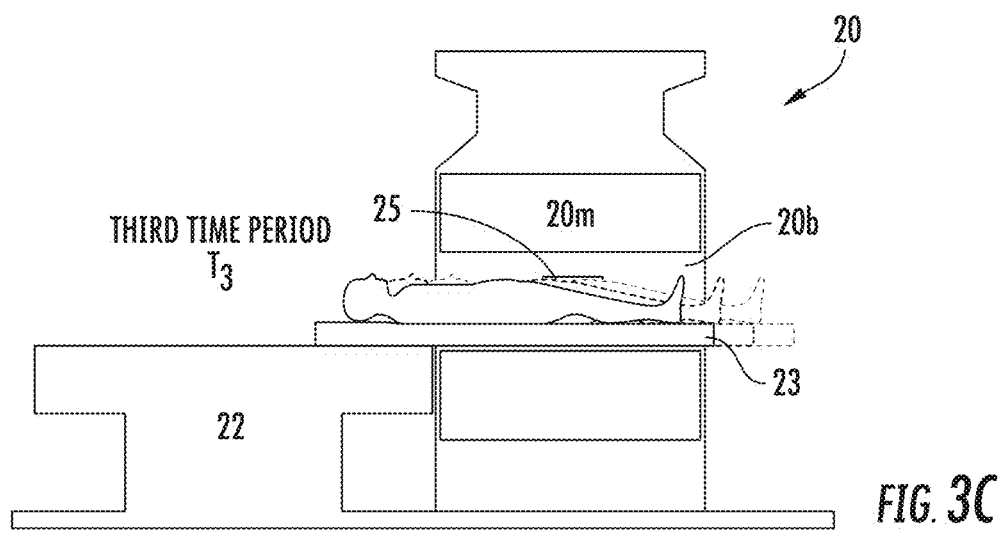

A scan duration is the time the patient spends inside the magnet to acquire all the defined planes (i.e., at least 4 planes: 3 short-axis and one long-axis). This can take as short as 4 heartbeats. In a representative case, described below, the imaging planes can have 6 planes, and the scan can take 6 heartbeats. The acquisition can be initiated by an operator, typically by pressing a "scan start button" to launch the strain encoding acquisition. Verbal or other launch initiation actions can be used. If the patient is outside the magnet, the scanning time can include an additional time period, such as about 20 seconds, for moving the patient into and out of the MRI magnet, making the whole scan time period, including patient movement into the bore of the magnet, between 60 seconds to about 30 seconds. A physician, a nurse, or an assistant ("clinician') can be inside the MRI room to monitor and manage moving the patient into and out of the magnet. An exemplary sequence for moving a patient is illustrated in FIGS. 3A-3C. FIG. 3A shows a patient moved into the magnet bore 20b during a first timer period T1. FIG. 3B shows image acquisition scan time T2 and FIG. 3C shows the patient is transported out of the magnet bore 20 during a third time period T3. T1+T2+T3≤5 minutes, typically between 25 seconds and 90 seconds, such as about 25 seconds, about 30 seconds, about 40 seconds, about 50 seconds, about 60 seconds, about 70 seconds, about 80 seconds and about 90 seconds.

Image Analysis

Figure 4:
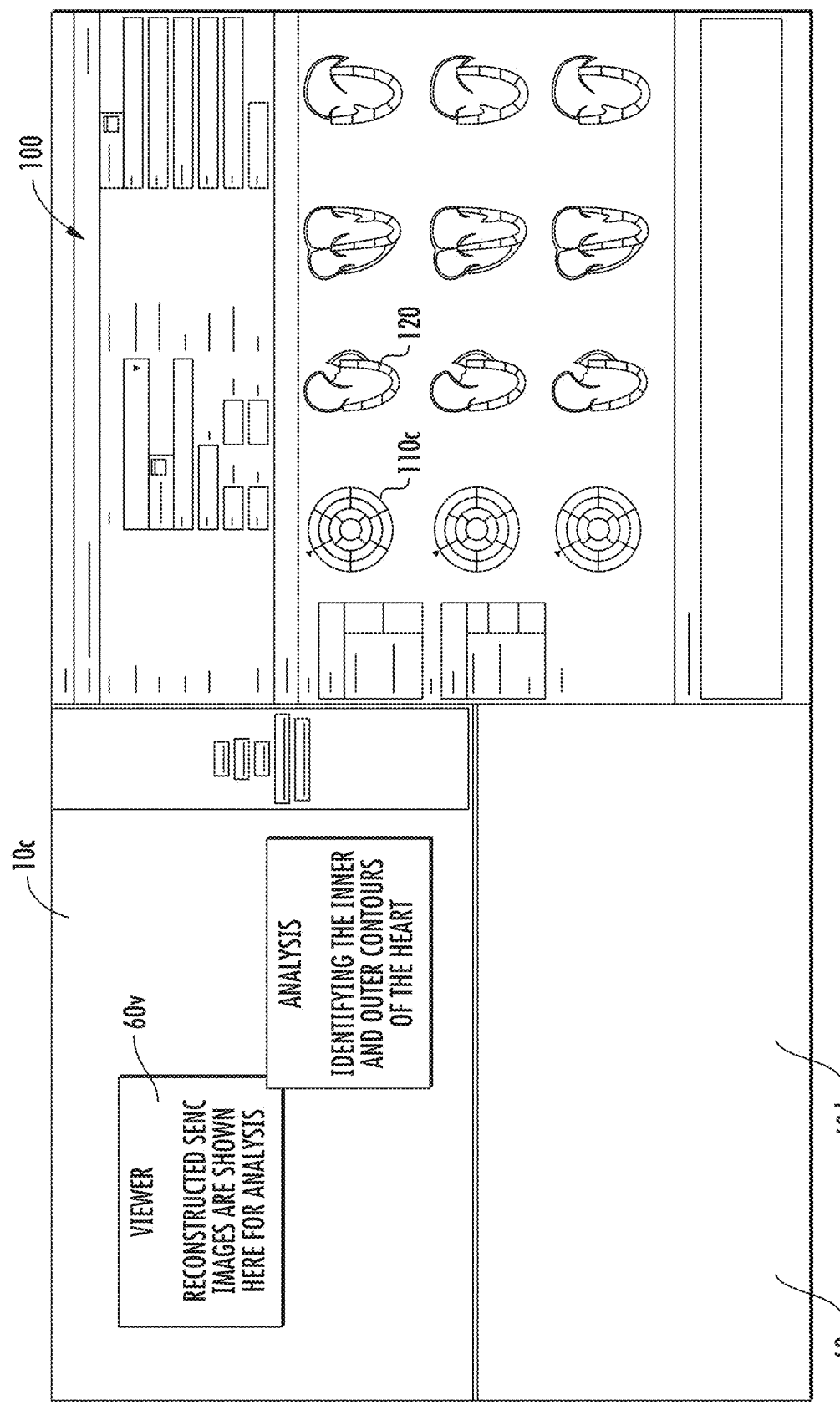
FIG. 4 is a schematic illustration of a circuit for image analysis that can generate a report/populate standardized compartmentalized long and short axis heart models with quantitative strain values according to embodiments of the present invention.

For a fast scan test, images can be transferred and analyzed rapidly (within a few minutes or less from signal acquisition) on a workstation 60, as illustrated in FIG. 4. This is done by reconstructing the strain and anatomy images from the SENC raw images, segmenting the tissue based on the anatomy images, and showing on at least one display 60d and/or electronic and/or paper report 100 the strain values on standard diagrams (compartmentalized models) of heart cuts/slices 110, 120. FIG. 4 illustrates a display 60d with a viewer 60v that has a circuit 10c that can reconstruct SENC images for analysis and analyze inner and outer contours of the heart in different slices used to populate the strain measurements in the report 100. The figure shows the layout of the tool to show the reconstructed images, segmenting on that view, and filling the diagrams on the right side of the layout.

Figure 5A:
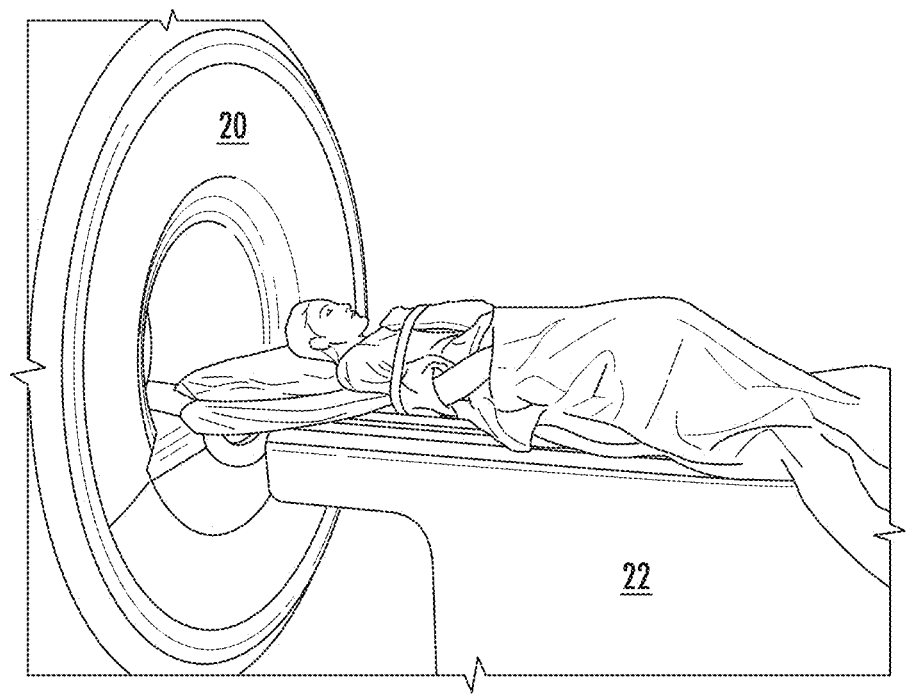
FIGS. 5A-5E are exemplary illustrations of outputs of an MRI scanner system with a workstation having a display with the cardiac models according to embodiments of the present application.
Figure 5B:
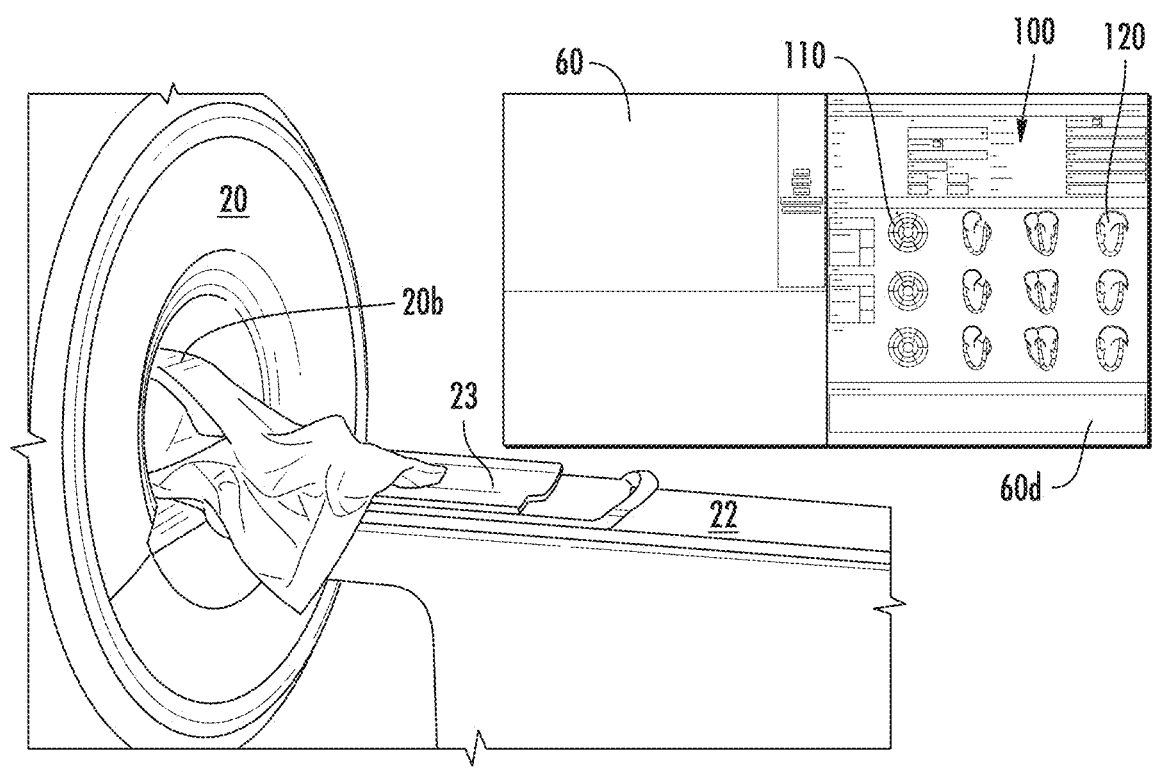
Figure 5C:
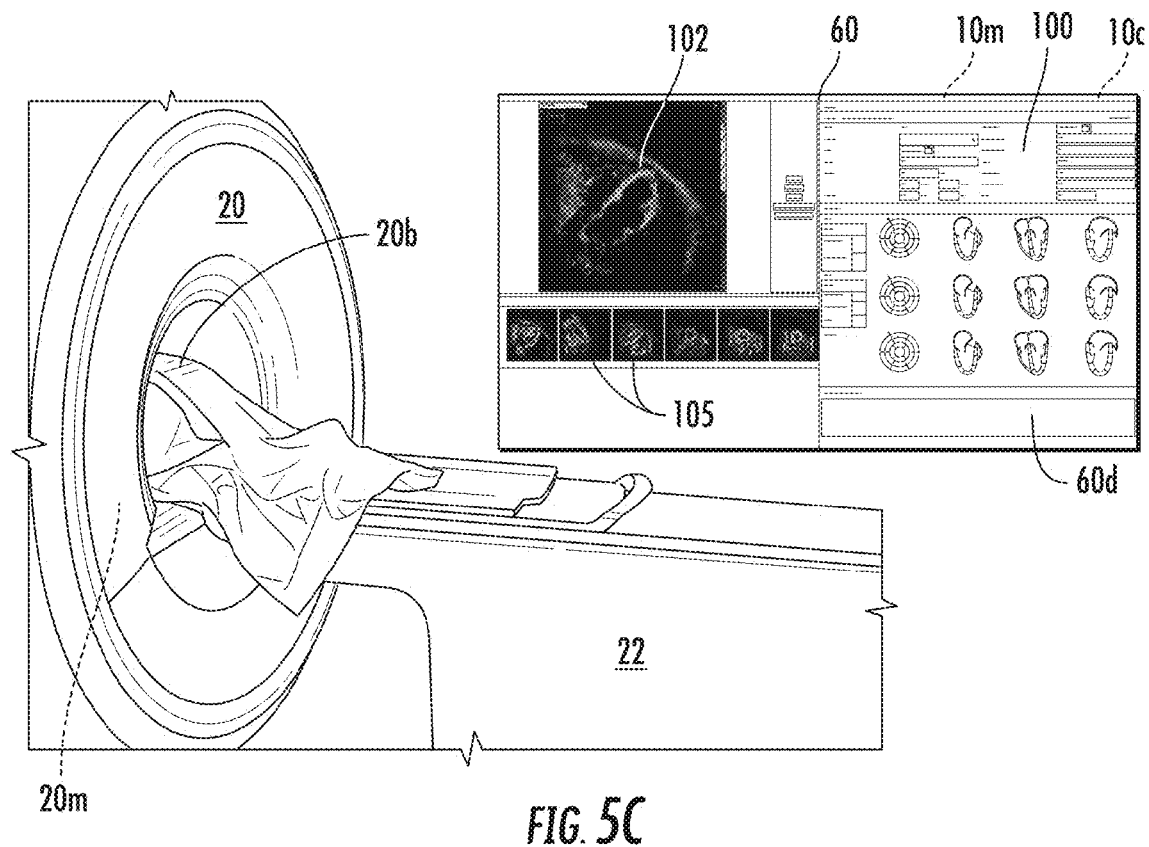
Figure 5D:
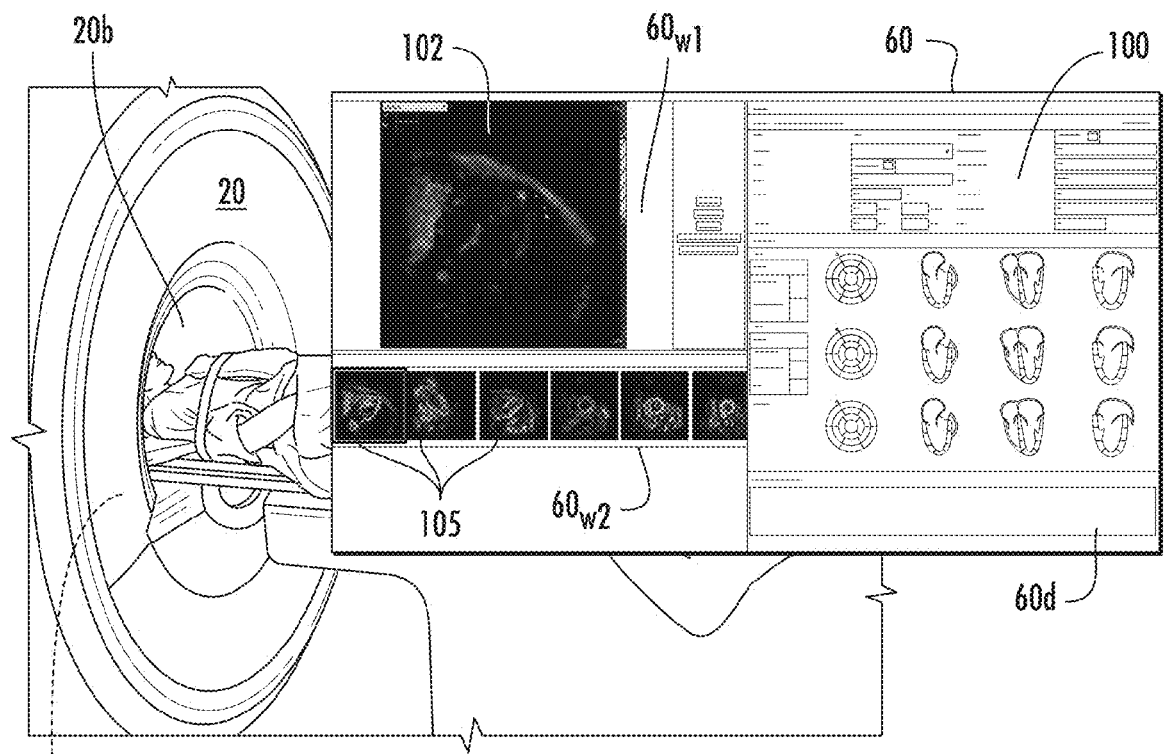
Figure 5E:
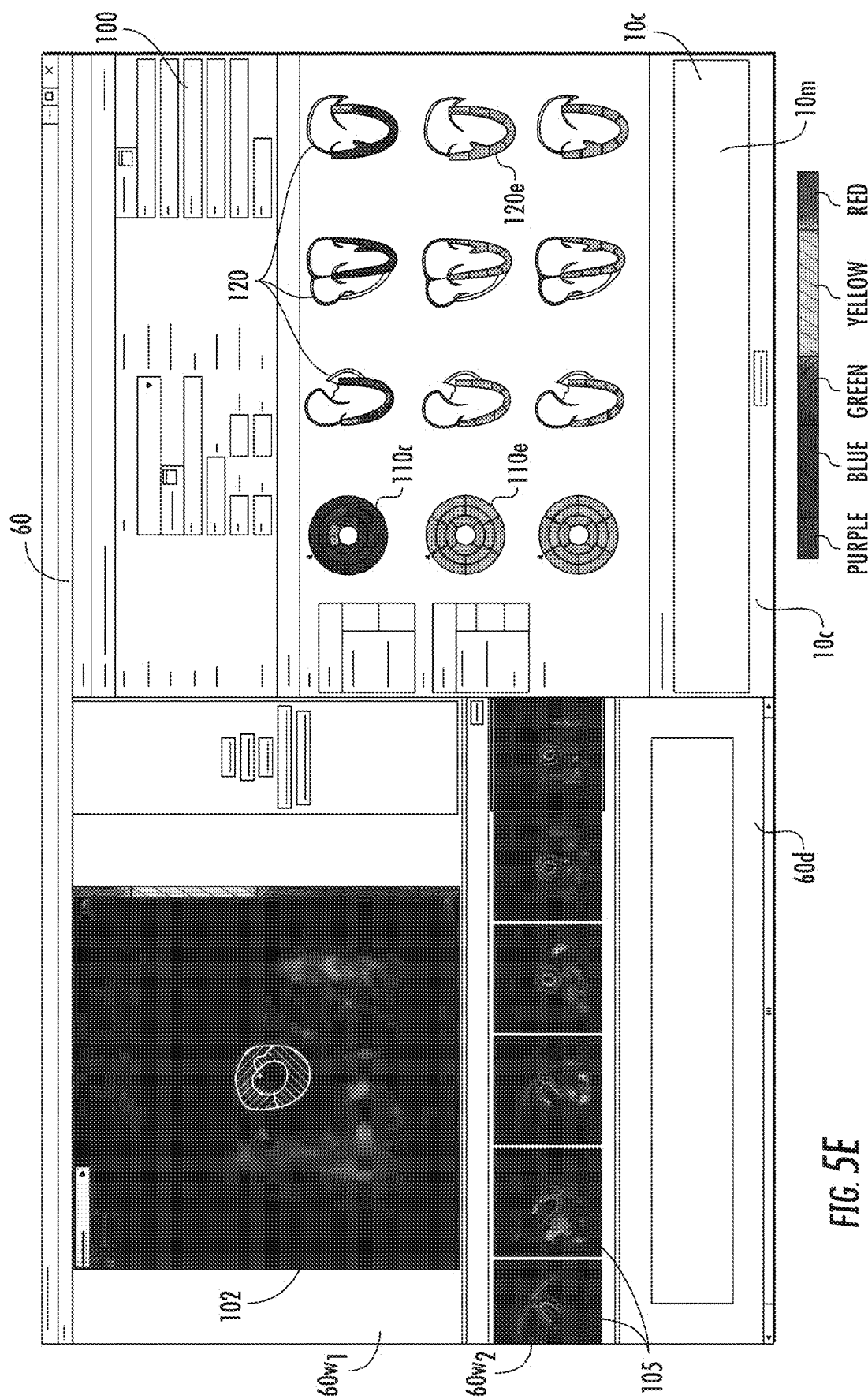

FIGS. 5A-E show illustrations of an MRI scanner system with a workstation 60 having a display 60d that can display a patient report 100 with the cardiac models 110, 120. FIG. 5A shows a patient on the scanner table 22 outside the MRI scanner 20 prior to acquiring the patient strain data. FIG. 5B shows the patient positioned within the bore 20b of the magnet, ready for data acquisition. FIG. 5C shows the cardiac evaluation module 10M and/or circuit 10c directing the scanner 20 to scan the heart for a plurality of strain sequences along individual planes through the heart. Scanning the heart for the imaging plane views (i.e., 4-6 views) of the heart (each producing a movie of the moving heart), can be carried out rapidly, typically takes less than 20 seconds, more typically 10 seconds or less. Once the strain sequences have been acquired, the scanner's table 23 can slide out bringing the patient out of the magnet 20m while the report 100 can be created. FIG. 5D illustrates the step of contouring one of the planes (window 60$w_1$ with the enlarged image(s) 102) to generate a strain sequence to evaluate circumferential strain, either manually or automatically, to define the heart chamber outline from which strain can be evaluated. Smaller cines or movies 105 of the 4-6 planes (shown as 6) can be provided in an adjacent window 60$w_2$. FIG. 5E illustrates contouring of a plane, either manually or automatically (enlarged view 102), to generate longitudinal strain within the defined chamber outline. A final strain report 100 showing all 6 strain sequences with final global and segmental strain values can be created in less than two minutes, typically 90 seconds or about 60 seconds (i.e., in about a minute) from when the last image signal acquisition from a patient is obtained so as to be generated in near-real time.

The term "segmental" refers to the ability to calculate different strain measurements for different cardiac tissue types of across different regions of a cardiac wall, i.e., myocardial, endocardial and epicardial, for example. Thus, segmental strain measurements can provide differential strain measurements across a wall for different tissue types, i.e., myocardial and one or both of endocardial and epicardial tissue.

SENC Outcome Reports

A report 100 with the resulting measurements from the analysis, including the conventional global measurements 130, and the regional measurements 101 of contractility, can be presented on a color-coded report as shown in FIG. 6. The figure shows the layout of the representative report showing the measurements, both global and regional, and marking the abnormal strain values in a defined color, typically in a red font type.

An appended color-coded graph 101g for the different tissue states can be provided on the report/display 100 to better delineate the actual strain values with level of myocardial contraction to differentiate normal from abnormal myocardial contraction as well as reversible from irreversible muscle weakening. Segmented 110s, 120s longitudinal and circumferential strain values can also be pictorially presented and color-coded to provide a relatively quick and easy evaluation of myocardial function.

Traditional measures 130 can be calculated and presented on the report, including ejection fraction, left ventricular mass, left ventricular end-systolic volume, left ventricular end-diastolic volume, and left ventricular stroke volume. Other measurements can be calculated from SENC strain imaging and added to the report.

The Actionable Strain Measurements

Figure 7:
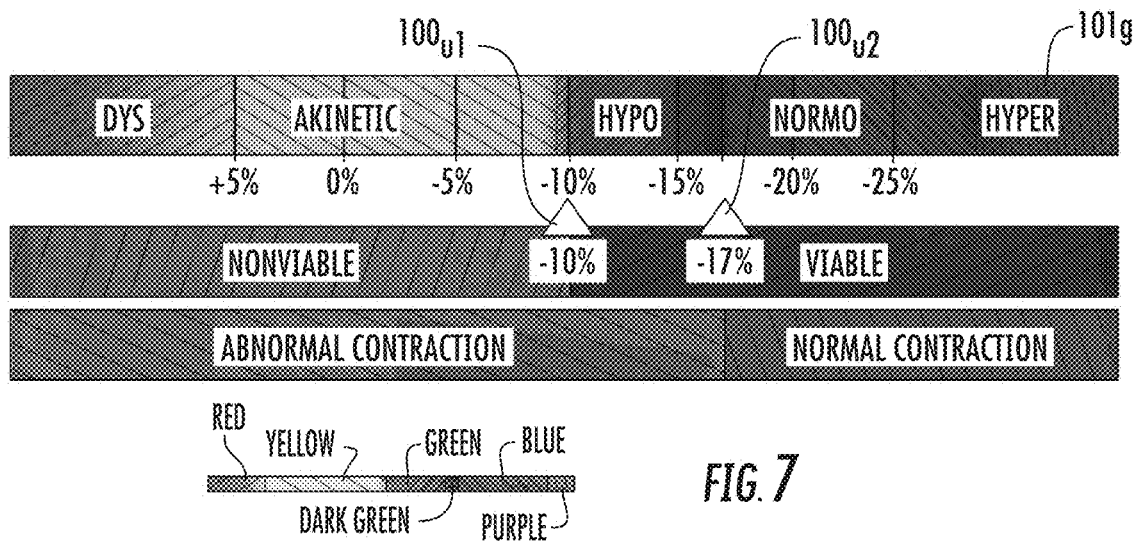
FIG. 7 is a graphic illustration of strain values versus heart condition/status according to embodiments of the present invention.

The strain measurements of the color-coded graph 101g can be presented in colors (shown in FIG. 7) reflecting, in general, the 5 states of the heart muscle: hyperkinetic, normokinetic, hypokinetic, akinetic, and dyskinetic. The strain measurements can be presented as negative numbers, indicating shortening of the wall muscle at maximum contraction.

The terms "strain measurement" and "measured strain" refers to any quantifiable measure of strain including one or more of strain rate, average and mean, for example. The measured strain can be segmental and/or regional or both segmental and regional.

The report can identify at least two important cutoffs:
Weak Cutoff: The cutoff separating normal or healthy muscle from muscle showing weaker contraction. The proposed value, shown in the figure, is the value −17%.
Reversibility Cutoff: The cutoff that indicates, in certain states of disease (such as myocardial infarction) whether the weakened muscle is temporarily weak and can recover, or permanently damaged and cannot recover (irreversible weakness). The proposed value, shown in the figure, is the value −10%.

The Weak Cutoff and the Reversibility Cutoff 100$u_1$, 100$u_2$ can both be "universal" cutoff values that are clinically valid across gender and different age groups from pediatric to geriatric.

Fully Automated Segmentation of MR SENC Images

Figure 8:
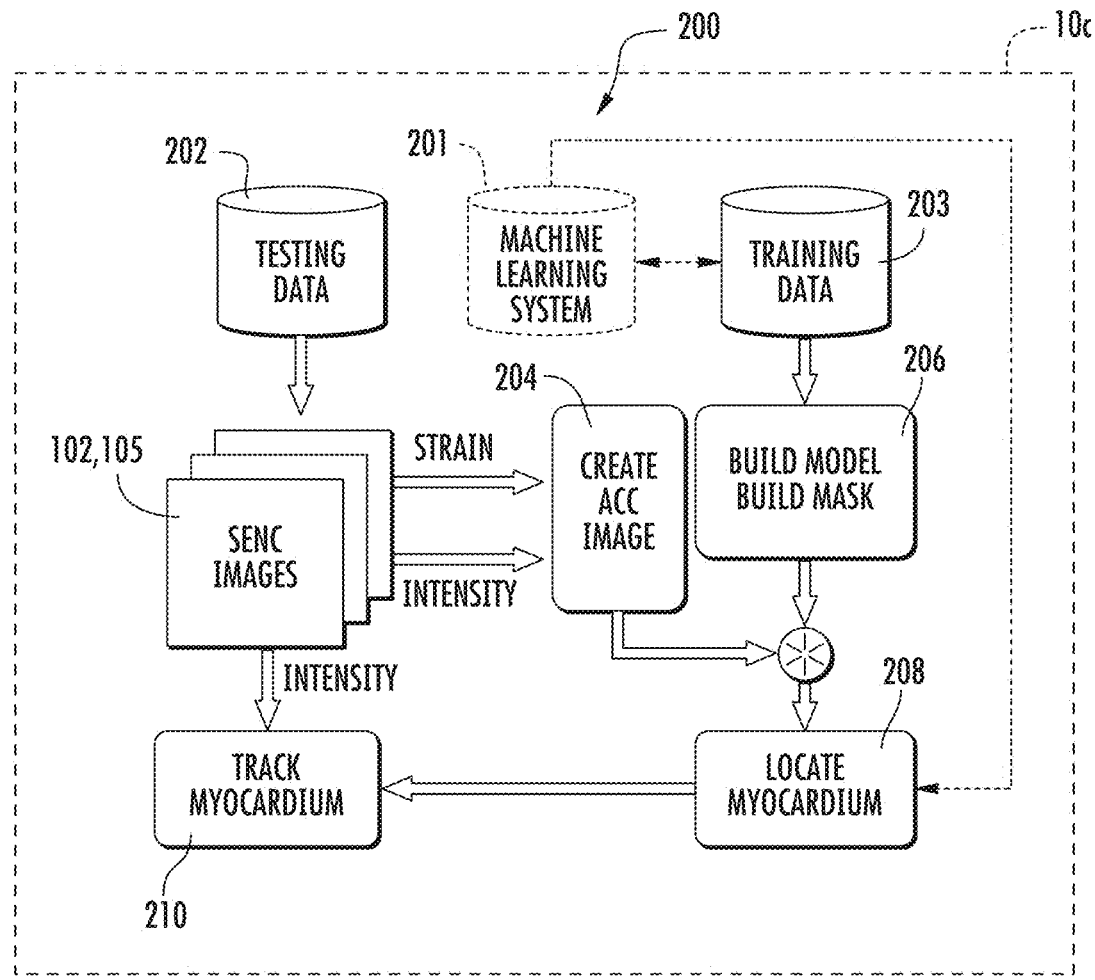
FIG. 8 is a block diagram of a flow chart of actions that can be carried out by a circuit (i.e., using at least one digital signal processor) for automated segmentation of MR SENC images according to embodiments of the invention.

Embodiments of the invention can employ a circuit 10c with at least one processor configured with a protocol/method to detect, segment and track myocardial muscle in four-chamber LA SENC and Fast SENC (e.g. FSENC)

images using ASM, which depends on PCA, to encode shape variations found in the training data. FIG. 8 shows an example of a flowchart with actions for the detection, segmentation and tracking of the myocardial tissue. Training data 203 can be used to build the myocardium model and the myocardium mask 206. Then, for every testing data 202, the circuit 10c can locate the myocardium 208 by analyzing the SENC images 102 and/or 105, (intensity and/or strain) creating an "ACC" image 204, and finally the circuit 10c can track the myocardium throughout the cardiac cycle 210 (i.e., using intensity).

FIG. 8 also illustrates that the circuit 10c may comprise a machine learning system 201 that can be used to identify the myocardium with or without the ACC image 204, models and masks 208, for example. The machine learning system 201 can be configured to use the training data 203. Machine learning systems are well known to those of skill in the art. See, e.g., H. Irshad et al., *Methods for nuclei detection, segmentation, and classification in histopathology: A review-current status and future potential*, IEEE Rev. Biomed. Eng., vol. 7, pp. 97-114 (2014), the contents of which are hereby incorporated by reference as if recited in full herein.

Figure 12:
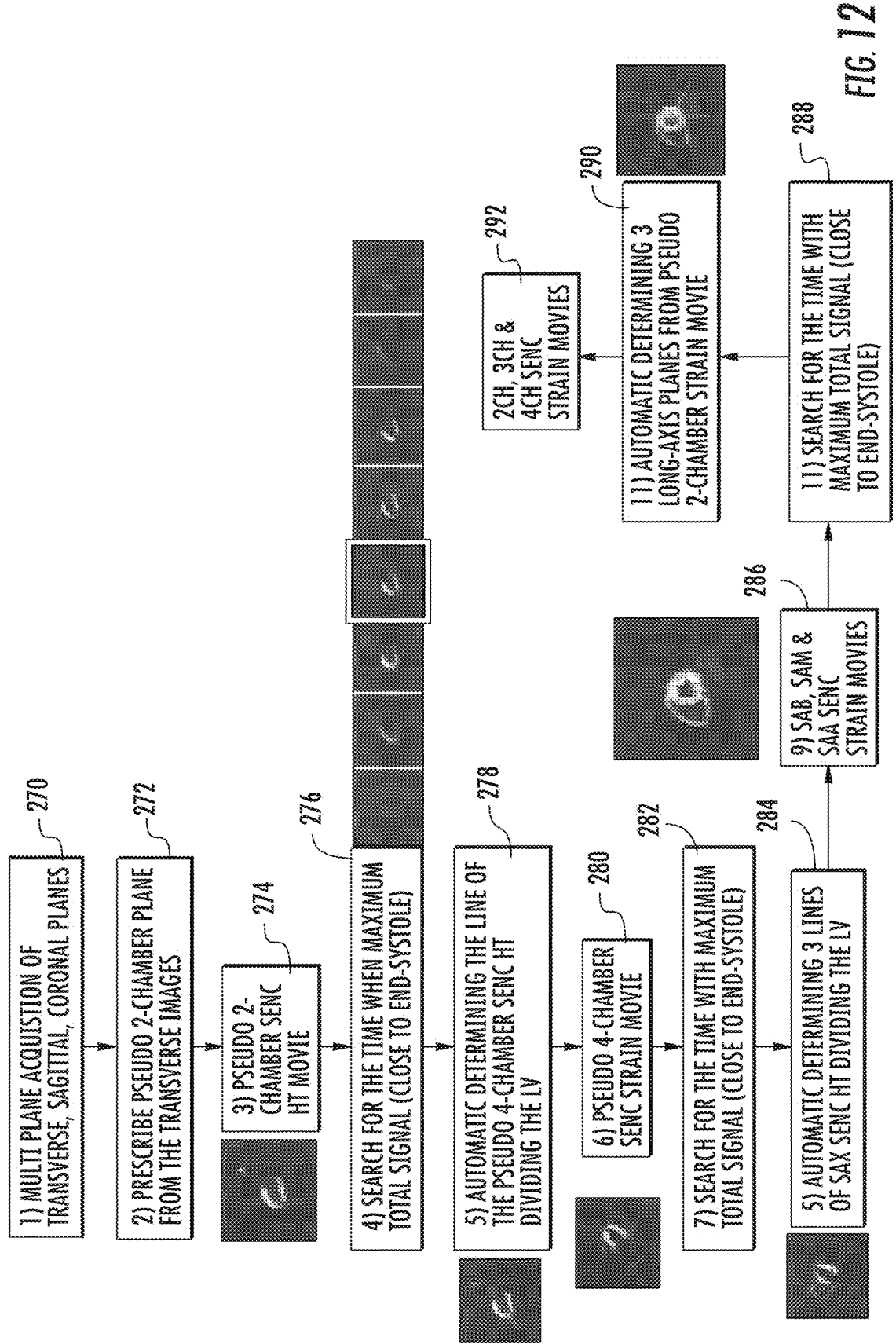
FIG. 12 is a graphic illustration of exemplary method actions for automatic planning (prescription) to find the same 6 planes similar to those obtained in FIGS. 11A and 11B according to embodiments of the present invention.
Figure 14:
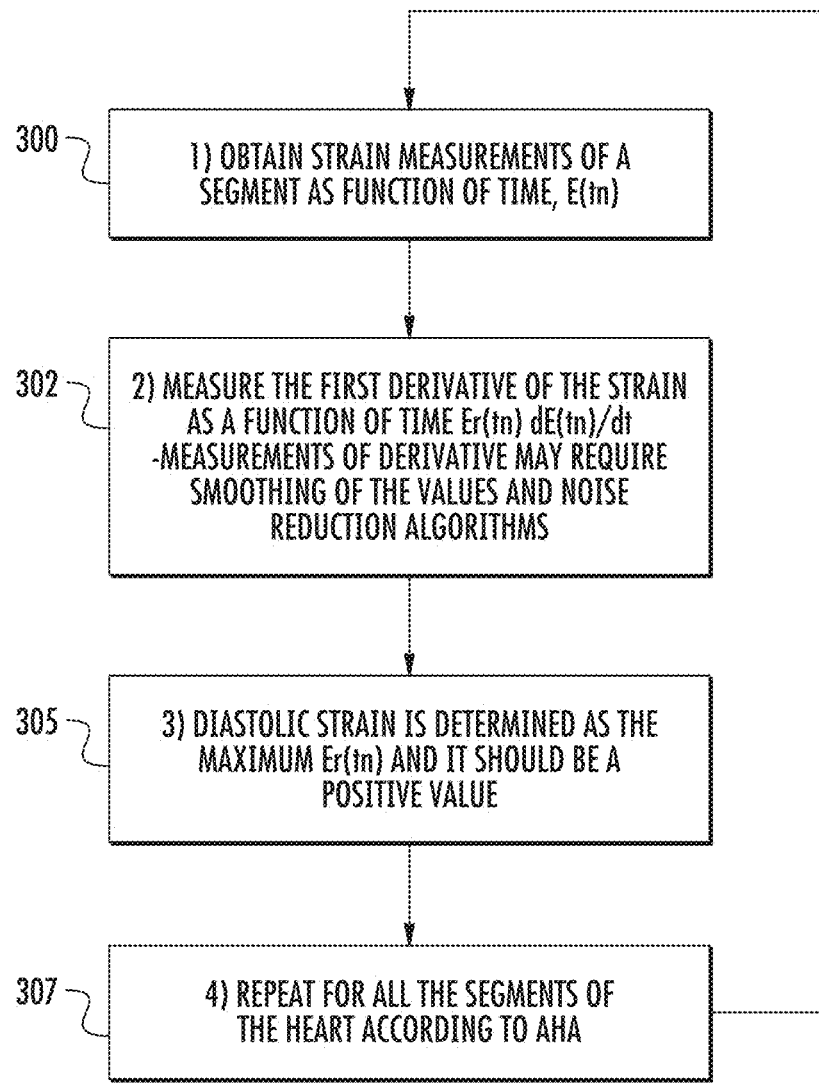
FIG. 14 is a block diagram of exemplary steps for quantifying diastolic dysfunction by measuring diastolic strain rate at different segments based on strain measurements obtained with SENC imaging according to embodiments of the present invention.
Figure 15:
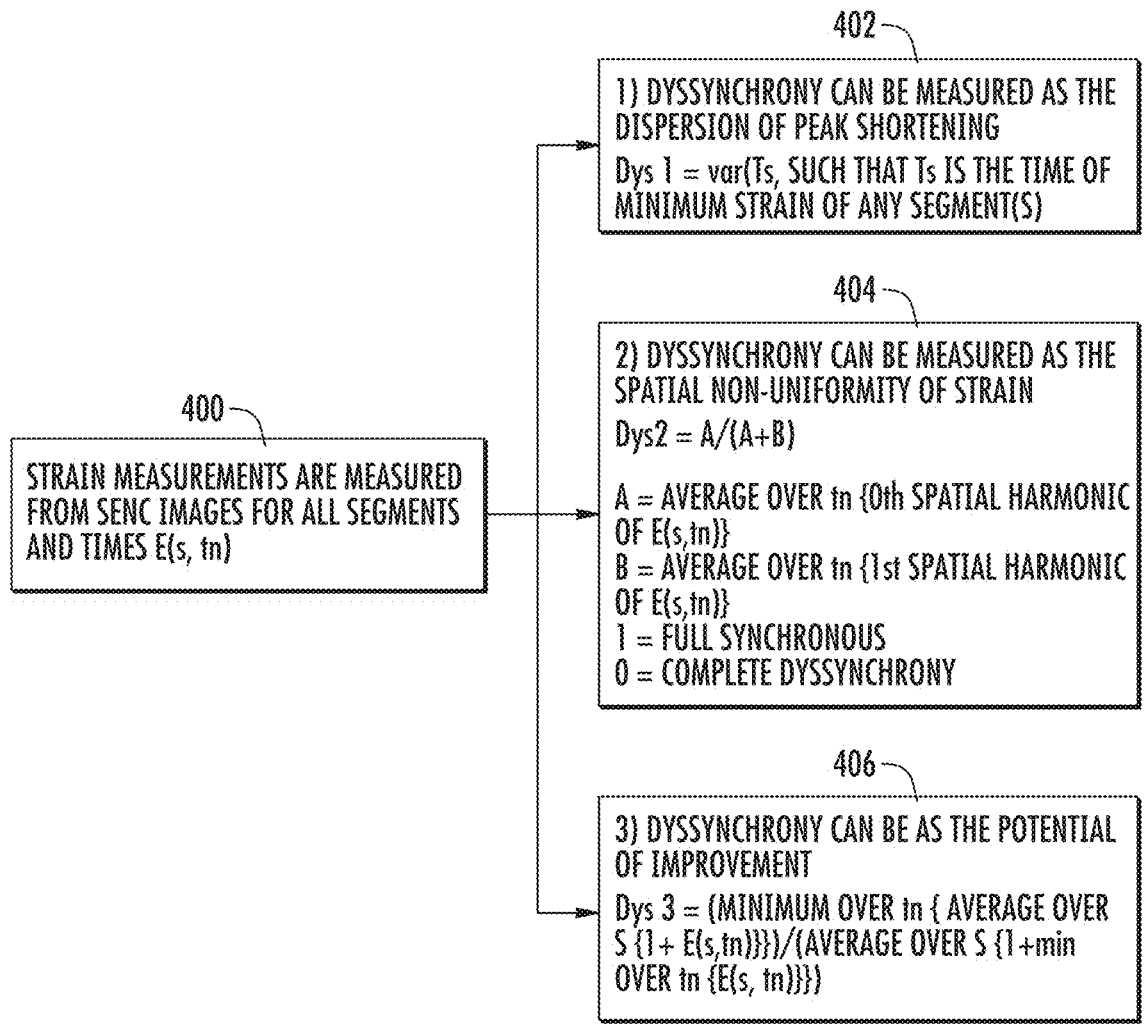
FIG. 15 is a block diagram showing three approaches for utilizing SENC strain mapping to measure heart contraction dyssynchrony from strain measurements obtained at different locations and different points of time according to embodiments of the present invention.

The methods of FIGS. 12, 14 and 15 may also incorporate or use machining learning systems (i.e., artificial intelligence systems) according to embodiments of the present invention.

Various exemplary steps for constructing an ACC image are shown in the A-H images/image frames of FIGS. 9A-H: 9(A) four frames of typical SENC images, 9(B) Images after applying opening by reconstruction, 9(C) Images after threshold, 9(D) ACC image, 9(E) strain information is used to detect chest wall, 9(F) Final ACC image, 9(G) mean shape X overlaid on the myocardium location after determining the maximum convolution value between Mask and ACC, 9(H) the mean shape X deforms to this specific patient myocardial shape.

See El Harouni, Ahmed, *Enhancing strain-encoded (SENC) MRI for breast and cardiac imaging*, The Johns Hopkins University, dissertation, 2011, 3463429, (Proquest Document View, http://gradworks.umi.com/34/63/3463429.html), the contents of which are hereby incorporated by reference for a discussion of exemplary Automated Segmentation with a Mask, Model and an ACC image. However, as will be appreciated by one of skill in the art other algorithms and/or machine learning systems may also be used for identifying the target tissue.

Fast Planning for Imaging Views

FIGS. 10A-C show SENC raw images 102r with a plurality of (shown as three) different cuts or planes 102c for fast automated planning of imaging views. Before the fast scanning for the fixed short- and long-axis views of the heart, there can be a preparation of placing the patient on the table and the localization of the heart and imaging views can be identified through this initial acquisition. To shorten this acquisition time and make it very fast, SENC raw images 102r can be used to determine these imaging planes. The advantage is the fast acquisition of the SENC raw images (a single heartbeat per sequence) that does not require breath hold. Images close to the maximum contraction of the heart (end systole) can be used to plan to the correct imaging views.

Figure 11A:
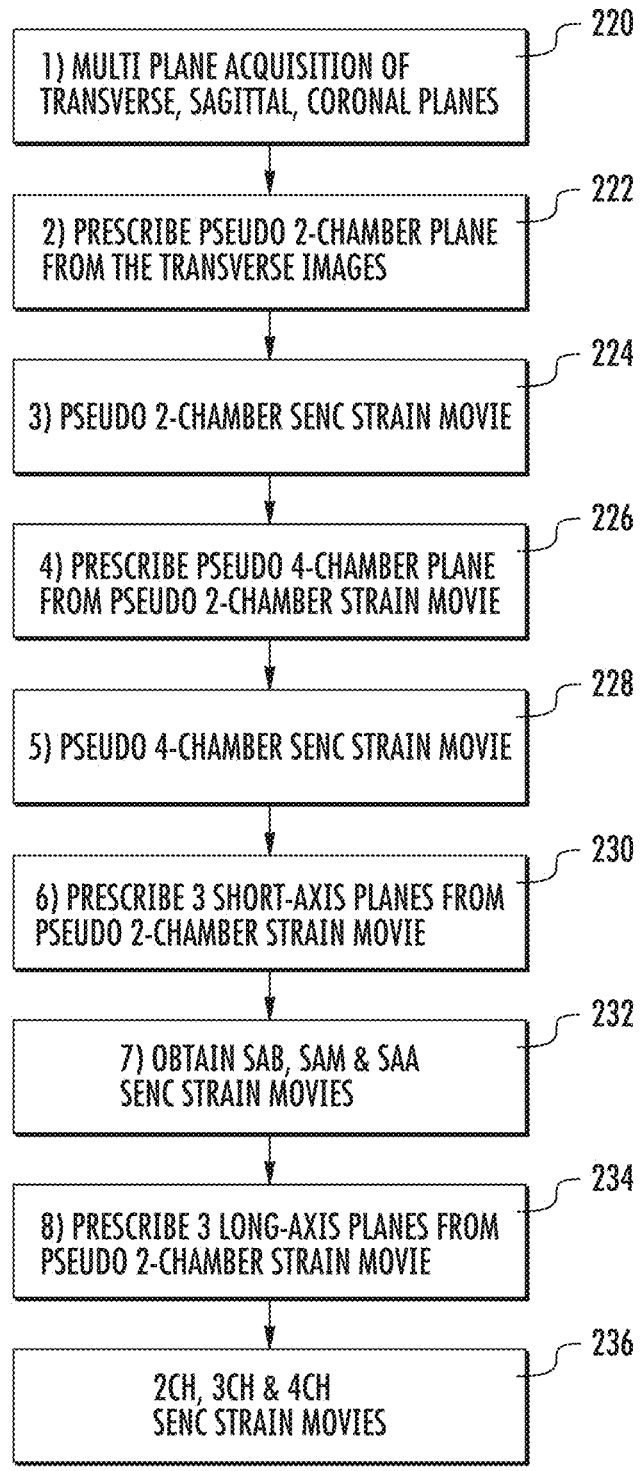
FIG. 11A is an illustration of a method with exemplary steps that can be taken for the MRI scanner to fast plan for imaging the heart using SENC strain images according to embodiments of the present invention.

FIG. 11A shows the steps taken by the operator of the MRI scanner to fast plan for imaging the heart using SENC strain images. The operator can save significant time and complexity by replacing the multiple conventional cine images of the heart, that each take at least one several seconds breath hold by SENC movies that take only a single heartbeat acquisition. Therefore, the prescription (planning) time is shortened significantly. At the end of the prescription, 4-6, typically 6, imaging (view) planes will be defined: 3 short-axis at the base, mid and apex of the left ventricle, and 3 long-axis views of the 2-chamber, 3-chamber and 4 chamber planes. Multi-plane acquisition of transverse, sagittal and coronal planes is obtained (block 220). Pseudo 2-chamber plane can be automatically prescribed from the transverse images (block 222). Pseudo 2-chamber SENC movie can be generated (block 224). A pseudo 4-chamber plane can be automatically prescribed from the pseudo 2-chamber strain movie (block 226). A pseudo 4-chamber SENC strain movie can be generated (block 228). Three (3) short axis planes can be automatically prescribed from the pseudo 2-chamber strain movie (block 230). SAB (short axis basal), SAM (short axis medial), SAA (short axis apical) SENC strain movies can be generated (block 232). Three (3) long axis planes can be automatically prescribed from the pseudo 2-chamber strain movie (block 234). Two chamber, three chamber and four chamber SENC strain movies can then be generated (block 236).

FIG. 11B shows the produced images by following the steps described by FIG. 11A. The first set of images (step 1) are the standard images acquired in any cardiac MRI exam to help in locating the heart. The bottom colored images with the appended graphs of intensity versus time are the SENC strain images obtained in steps 2 (block 222), 4 (block 228) and 6 (block 232). The prescription planes P are defined by the white thick lines inside the images.

The term "pseudo" in the case of cardiac MRI imaging means that the view of the heart is approximate to the actual view. The concept is that in order to reach a standard view of the heart (3 chamber, 4 chamber, 2 chamber) using MRI, some preliminary MRI images, which can be presented as movies of cuts of the heart, can be obtained to determine the orientation of the heart. The first "approximate" 2 chamber view of the heart may not be very accurate (that is why it is called pseudo 2 chamber in FIGS. 11A and 11B), but it can be an important view to find a "true" 2 chamber view of respective patients in the bore of the magnet.

Alternatively, the evaluation described with respect to FIGS. 11A and 11B can start with a pseudo 4 chamber plane and images, then obtain the pseudo 2 chamber plane and images. In general, current cardiac MRI planning images to identify the position and orientation of the heart can be modified to use SENC strain images that replace the conventional cine (movie) images.

"ACC Image" means Accumulate Image
"ASM" Active shape model
"AAM" Active Appearance Model
"SAB" Short-axis Basal
"SAM" Short-axis Medial
"SAA" Short-axis Apical Fully-Automated Planning for Cardiac MRI The SENC fast pulse sequence can be used to automate the planning phase of imaging, which is the initial step in any cardiac MRI exam. Planning using SENC can have two steps: 1) locating the heart to delineate the position of the heart relative to other anatomy within the imaging field of view; and 2) determining the orientation of the ventricles to define the principal axes of the heart.

The preparation for any cardiac acquisition can be automated using the single heartbeat SENC acquisition to avoid lengthy, manual planning of the planes prior to any SENC test or conventional cardiac MRI to shorten the time of imaging. Automated planning also will allow patient movement in between scans to avoid claustrophobia by shortening scanning segments, allow interventions such as contrast or other agent injections without worrying that movement of the patient may ruin the entire imaging if the patient doesn't return to the exact spot, or allow patient movement to mechanically increase contractility and/or heart rate to stress the heart and observe changes in heart movement to identify wall motion abnormalities.

FIG. 12 shows exemplary steps for automatic planning (prescription) to find the same 6 planes similar to those obtained in FIGS. 11A and 11B without manual positioning or principal axes definition. The automatic planning leverages SENC imaging's ability to quickly and reliably identify the contracting heart by its brightness in the high tuning (HT) images. The steps mirror those of the manual approach but with the use of an object recognition algorithm to identify the heart. The only manual interaction that may, in some embodiments, be used, can be an identification of the best transverse view of the heart from the multi plane acquisition to start the automated planning steps.

Multi-plane acquisition of transverse, sagittal and coronal planes is performed (block 270). A pseudo two-chamber plane can be automatically prescribed from the transverse images (block 272). A pseudo 2-chamber SENC HT movie is obtained (block 274). A time for maximum total signal is identified in a frame of the movie as associated with close to end-systole (block 276). This is shown by a highlighted perimeter of a medial frame. Automatically determining a line of the pseudo 4 chamber SENC HT dividing the LV (block 278). Obtaining a pseudo 4-chamber SENC strain movie (block 280). A time for maximum total signal is identified in a frame of the movie (associated with close to end-systole)(block 282). Automatically determining three lines of short axis SENC HT dividing the LV (block 284). SAB, SAM and SAA SENC strain movies are obtained/generated (block 286). A time for maximum total signal is identified in frames of the movies (associated with close to end-systole)(block 288). Automatically determining three long axis planes from the pseudo 2 chamber (or 4-chamber) strain movie (block 290). Generate the two chamber, three chamber and 4 chamber strain movies (block 292).

Stress Testing with SENC Strain Imaging Fast Scans

Embodiments of the invention include stress exams that can be performed using multiple fast SENC strain imaging scans of the heart, at least one at rest and at least one in a different degree of stress to detect ischemia characteristic of coronary artery diseases. The stress test can also show improvement in myocardial function, characterized by a decrease in strain, under stress demonstrating viability in patients who have weakened myocardial contraction at rest.

Fast scans utilizing SENC strain imaging can assess ischemia in patients with coronary artery disease by comparing the SENC strain sequences under stress vs at rest. The fast scan can acquire SENC strain sequences to measure segmental function of the heart at rest, then the measurements will be repeated for the heart under stress. The stress component of the test can utilize any form of exercise that can induce wall motion abnormality in case of ischemia, or pharmacological agents that will have the same effects (e.g. dobutamine and adenosine).

Stress testing can utilize any non-pharmacological or pharmacological stressors. SENC strain imaging with its higher sensitivity requires less stress to accurately identify ischemic myocardium thus shortening the acquisition time, exposing the patient to far lower levels of stress, and reducing the risks of eliciting a stress response. This enables identifying ischemia through administration of much smaller doses of pharmacological agents (e.g. dobutamine, adenosine, etc.), utilization of less risky agents that evoke a lower stress response, and/or incorporation of non-pharmacological mechanisms such as treadmill, Valsalva maneuvers, minimal exercise of the upper or lower body with the patient in supine position remaining on the table to expedite SENC imaging.

Many types of exercises that produce a low level increase in stress from rest may be utilized to cause a mild increase in contractility from which the changes in SENC strain from rest to stress can determine an ischemic effect. For example, patients may utilize a modified stair stepper or bicycle so the patient can remain lying on the table while exercising to raise their heart contractility. Alternatively, modified weights such as elongated balloons filled with sand or water or hand grips that provide tension when squeezed may be utilized as exercise to increase contractility. The increase in contractility may be partially correlated with an increase in heart rate to identify the timing from which the stress strain sequences should be acquired. For example, a heart rate increase of 10-20 beats per minute (bpm) is associated with a corresponding increase in contractility from which SENC stress testing can detect an ischemic response.

The ability to tailor the type of stress testing medium to patients needs accommodates differences in patient tolerance to pharmacological agents, ability to walk or exercise while standing up, frailty in exertion due to underlying comorbidities, or other condition that allows the physician to choose a specific stress medium.

The Stress Outcome Report

Figure 13A:
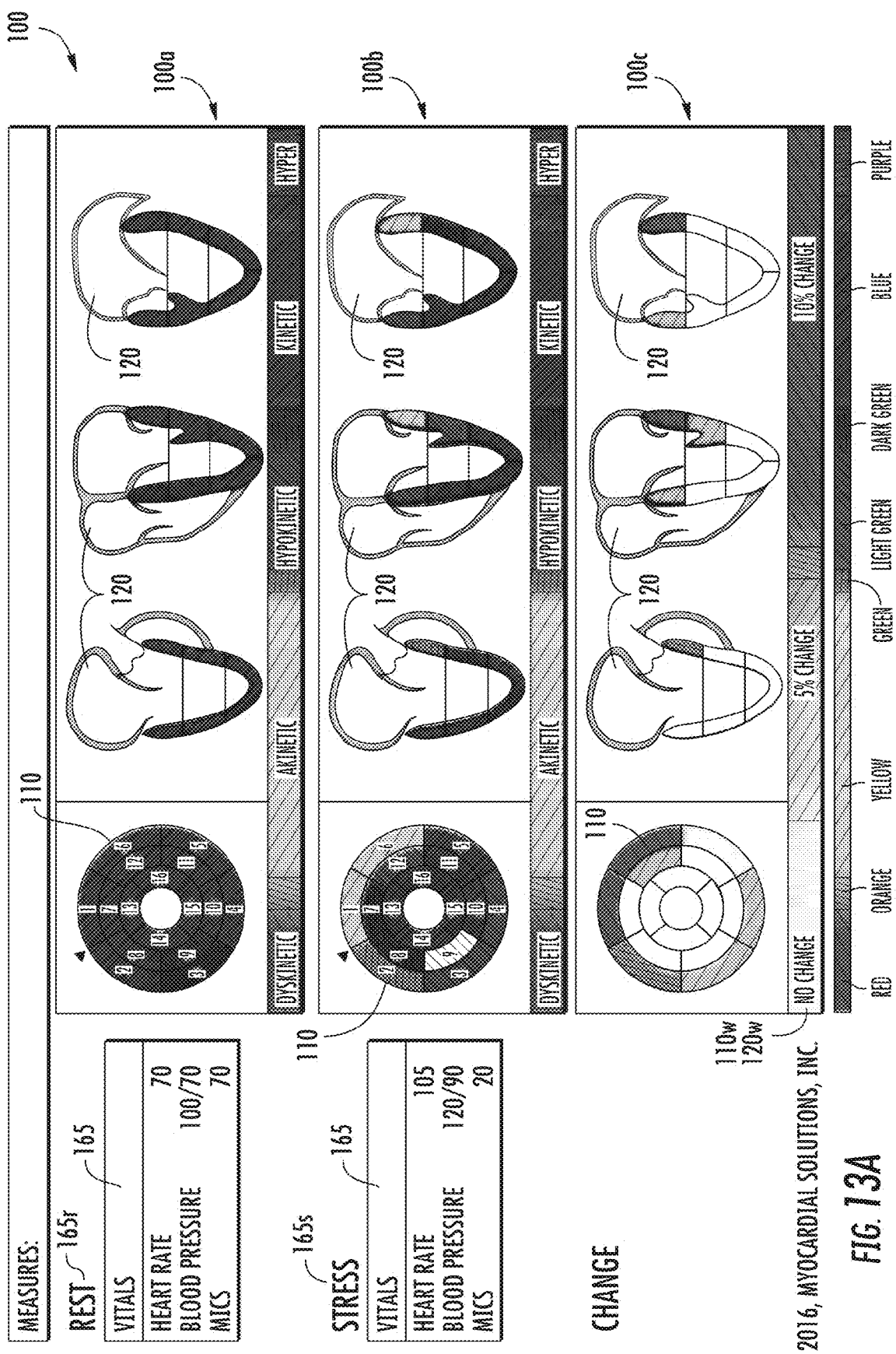
FIG. 13A is an illustration of a stress outcome report with a fast scan at rest (top row), at stress (second row) and a third row with the compartmentalized heart models populated by a change in the strain values between the first and second rows which may be particularly useful to indicate potential ischemia according to embodiments of the present invention.

The stress report 100, shown in FIGS. 13A & B, can show the strain measurements obtained with the fast scan at rest 100a (first row) and under stress 100b (second row) and the change in strain measurements 100c (third row) to show regions in heart models 110, 120 with potential ischemia, an indication of coronary artery stenosis. The color coding in these two representative examples show different representative ways to graphically delineate myocardial contraction based on strain measurement values.

FIG. 13A shows a stress report 100 in which the absolute change in strain is determined by subtracting $strain_{stress}$ (the strain at stressed condition) minus $strain_{rest}$ (the strain at rest) and ranges from 0% to 10% to delineate ischemia. Changes in strain in the models 110, 120 in the change set of models 100c that identify viability (negative numbers with this calculation) can be lighter, such as shown as white in associated compartments 110w, 120w with the value set to 0%. Patient vitals 165 (heart rate and blood pressure) at rest 165r and stress 165s can be provided adjacent the heart models for these conditions, 100a, 100b, respectively.

Figure 13B:
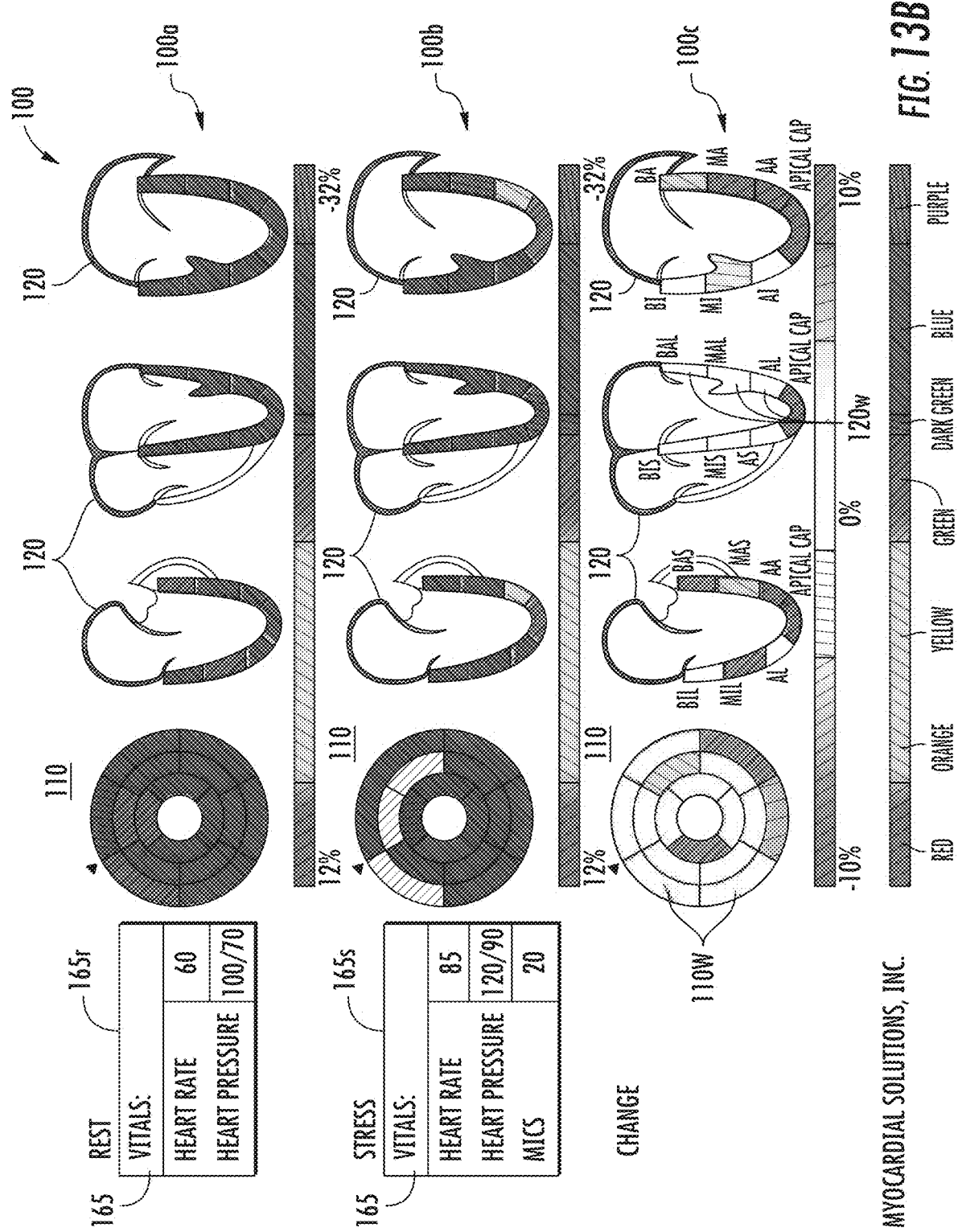
FIG. 13B is an illustration of an alternative stress outcome report with a different color-coding so that the stress test not only calculates changes in strain between rest and stress conditions that indicate potential ischemia, but also includes improvement in strain (decrease in strain values) under stress that identifies myocardial viability according to embodiments of the present invention.

FIG. 13B modifies the calculation to identify myocardial viability and distinguish it from ischemia. In this embodiment, the absolute change in strain was calculated by subtracting $strain_{rest}$ minus $strain_{stress}$ and color coding positive changes (delineating myocardial viability due to a decrease in strain, improved contraction, from rest to stressed condition) in gradients of defined colors such as, for example, green and negative changes (delineating myocardial ischemia due to an increase in strain, worse contraction, from rest to stressed condition) in gradients of red with white demonstrating no change in strain from rest to stressed condition.

However, other defined colors can be used, such, as but not limited to, red and blue rather than red and green or other color differentiation to reflect weakening or strengthening of strain, respectively.

Advantages of the Fast Scan in Stress Test

By comparing multiple fast scans at rest and different levels of stress as described above, changes in contractility induced by ischemic disease and/or improvement in myocardial viability can be identified. The advantages of SENC strain imaging for stress testing include:

Non-Invasive Stress Exams
  The stress can be done using physical exercise with modest increase in contractility.
  SENC strain imaging enables stressing the patient to a minimal level of change in contractility to detect ischemic effects without having to inject agents into the patient to artificially evoke a stress response.
  The non-invasive SENC stress testing technique reduces procedure time, patient preparation, and patient recovery since needles and/or catheters do not need to be inserted and removed, and the effects of pharmacological agents do not need to be monitored before, during, and after.
  The non-invasive SENC stress testing mitigates risks of using pharmacological agents to evoke an increase in contractility since known adverse reactions to drugs can be avoided.
Less Risky Pharmacological Agent Regimens
  SENC stress testing can be induced using low doses of pharmacological agents or agents that evoke a minimal stress response.
  Reducing the pharmacological dosage required to evoke an increase in contractility to which an ischemic response can be identified, improves patient comfort, mitigates risks of administering high doses of pharmacological agents in diseased patients, and improves productivity and expediting patient recovery after the procedure.
Low Stress
  Low stress physical actions may also or alternatively be used and heartbeat rates are not required to be elevated to the same level as conventional stress tests.
Standardized Report Indicating Induced Wall-Motion Abnormality
  A coloring scheme is used to detect reduction of contractility of some heart muscle under stress, indicating lack of blood perfusion associated with coronary artery disease.
  The standardized report quantifying changes in strain scans eliminates subjectivity of the reviewer looking for subtle changes in motion of the heart muscle by eye.
  Directly measuring the strain of the heart muscle itself provides a better indicator of myocardial deformation.
  Being able to compare strain scans at rest versus under stress provides the ability to differentiate between ischemic myocardium versus non-viable, infarcted myocardium.

Quantifying Diastolic Dysfunction with SENC Imaging

While the embodiments of the invention using SENC to measure strain to evaluate contractility of heart muscle during systole have been described above, another metric is can be used to evaluate the relaxation of heart muscle during diastole. Embodiments of the invention also measure strain rate during the relaxation phase of the heart in the same segments used to calculate strain values during systole. These measurements show a different property of the heart muscle, which is stiffness that can be related to diastolic heart problems.

Strain Rate Measurements

FIG. 14 shows exemplary steps to measure the diastolic strain rate from strain measurements obtained at different segments and different times of the cardiac cycle. The strain rate is obtained from the temporal derivatives of the strain curves and measuring the maximum positive strain rate that determines the rate of stretching of the myocardium during diastole. Methods for reducing noise and curve fitting can be used to reduce the noise effect on measuring the derivatives.

Strain measurements are obtained of a segment as a function of time, $E(t_n)$ (block 300). The first derivative of strain is measured as a function of time $Er(t_n) dE(t_n)/dt$ (block 302). Measurements of derivative can include smoothing of the values and noise reduction algorithms. Determine diastolic strain as a maximum $Er(t_n)$ and this should be a positive value (block 305). Blocks 300-305 can be repeated for all segments of the heart according to AHA (American Heart Association) standardized models (block 307).

From the strain movies obtained, the rapid relaxation of the heart muscle during the ventricles' filling can be measured from the rate of change of the measured strain at different segments of the heart muscle during the filling. These relaxation strain rate will reflect the stiffness of the ventricles associated with some cardiac diseases. Measuring strain rate during diastole directly measures spatial deformation of the muscle which can be correlated to relaxation. Identifying patients with a minimum diastolic strain rate $<-31$ sec$^{-1}$ identifies patients with myocardial dysfunction who are at risk of diastolic heart failure [Neizel Y, et al. Impact of Systolic and Diastolic Deformation Indexes Assessed by Strain-Encoded Imaging to Predict Persistent Severe Myocardial Dysfunction in Patients After Acute Myocardial Infarction at Follow-Up. J Am Coll Cardiol 2010; 56:1056-62]. The contents of which are hereby incorporated by reference as if recited in full herein.

Evaluating Dyssynchrony in Contraction with SENC Imaging

Embodiments of the invention also measure temporal differences in strain and/or strain rate between various chambers of the heart or throughout a single heart chamber to identify dyssynchrony and predict the impact of various management algorithms on improvement in myocardial function. Evaluating the time difference between peak strain, which is associated with tissue deformation during systole, or calculating circumferential uniformity ratio estimate [CURE] index values for patients with left bundle branch block and/or patients with transmural infarcts can be used to determine heart failure that may benefit from resynchronization therapy and/or other intervention that address the delay in myocardial contraction.

FIG. 15 shows three exemplary approaches to measure dyssynchrony from strain measurements obtained at different locations and different points of time. Measuring strain throughout the cardiac cycle and optimizing predicted ejection fraction improvement by altering the timing of contraction of various chambers and/or throughout the chambers themselves can estimate the likelihood of treatment success utilizing various modalities to identify responders and/or guide the strategy of placement of leads or other stimulation modality to optimize synchrony and contraction of the heart.

Strain measurements are measured from SENC images for all segments and times $E(s, t_n)$ (block 400).

Dyssynchrony can be measured as the dispersion of peak shortening.

$Dys1 = \text{var}(Ts)$, such that $Ts$ is the time of minimum strain of any segment($s$) (block 402).

Dyssynchrony can be measured as the spatial non-uniformity of strain.

$Dys2 = A/(A+B)$

A = average over $t_n$ {0th spatial harmonic of $E(s, t_n)$}
B = average over $t_n$ {1st spatial harmonic of $E(s, t_n)$}

1=full synchronous
0=complete dyssynchrony
(block 404)

Dyssynchrony can be as the potential of improvement $Dys3$=(minimum over $t_n$ {average over $s$ {1+$E(s,t_n)$}})/(average over $s${1+min over $t_n${$E(s,t_n)$}}) (block 406)

SENC Imaging Applications and Decision Trees

The distinctive element of SENC testing involves the unique ability to quantify myocardial deformation by directly measuring strain using magnetic resonance imaging. This measurement identifies the level of myocardial contraction and provides an indication of weakening of heart muscle which precedes heart failure.

SENC Applications for Systolic Heart Failure

Figure 16:
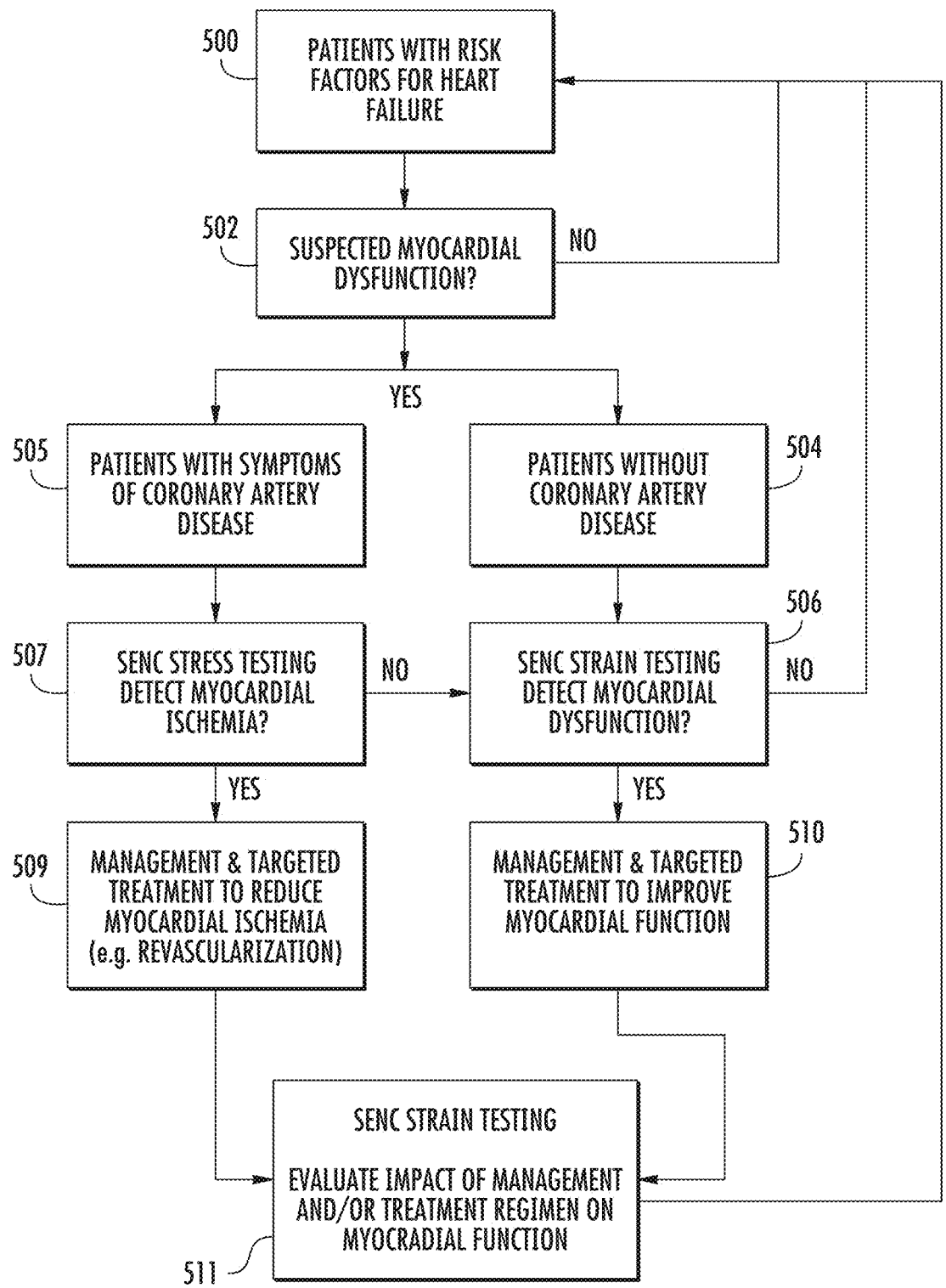
FIG. 16 is a block diagram of an exemplary decision tree to utilize SENC testing for screening and managing patients with risk factors of heart failure according to embodiments of the present invention.

FIG. 16 shows a decision tree to utilize SENC testing for diagnosing and managing patients with risk factors of systolic heart failure. Patients who are susceptible to myocardial dysfunction that puts them on the progressive path towards heart failure can be evaluated with SENC testing.

Patients with Risk Factors for Heath Failure are identified (block 500)
Suspected Myocardial Dysfunction? (block 502)
Patients without Coronary Artery Disease (block 504)
Patients with Symptoms of Coronary Artery Disease (block 505)
SENC Strain Testing Detect Myocardial Dysfunction? (block 506)
SENC Stress Testing Detect Myocardial Ischemia? (block 507)
Management & Targeted Treatment to Reduce Myocardial Ischemia (e.g. Revascularization) (block 509)
Management & Targeted Treatment to Improve Myocardial Function (block 510)
SENC Strain Testing. Evaluate Impact of Management and/or Treatment Regimen on Myocardial Function (block 511)

Patients with symptoms or indicators of coronary artery disease can be tested with SENC strain imaging at rest and under stress from pharmacological agents or completely non-invasive methods such as exercise, maneuvers such as Valsalva, or other techniques that increase contractility. As discussed above, the difference in strain measurements at rest and under stress identifies myocardial ischemia and/or myocardial viability. The extent of myocardial ischemia correlates to coronary stenosis and indicates the need for further evaluation and potential revascularization through percutaneous coronary intervention or bypass grafting. Improved strain in weakened myocardium under stress (e.g. decrease in strain from rest to stressed condition) identifies myocardial viability since it characterizes improved myocardial contraction under stress despite showing weakened myocardial contraction at rest.

SENC stress testing also generates a strain map that delineates myocardial dysfunction identifying weakened myocardium that may result from a prior infarction or other comorbidity that reduces contractility of the myocardium. The stress and strain maps guide management or targeted treatment of the patient based on the extent and location of ischemia and myocardial dysfunction. After revascularization or medical management, in cases where intervention is not warranted, the impact of treatment on myocardial function is evaluated by repeat strain mapping to determine heart remodeling and improvement in myocardial contractility.

Patients without symptoms or indicators of coronary artery disease or those in which ischemia is ruled out are evaluated for myocardial subclinical dysfunction with strain mapping. The extent of myocardial dysfunction is used to direct management and tailored treatment.

Figure 17:
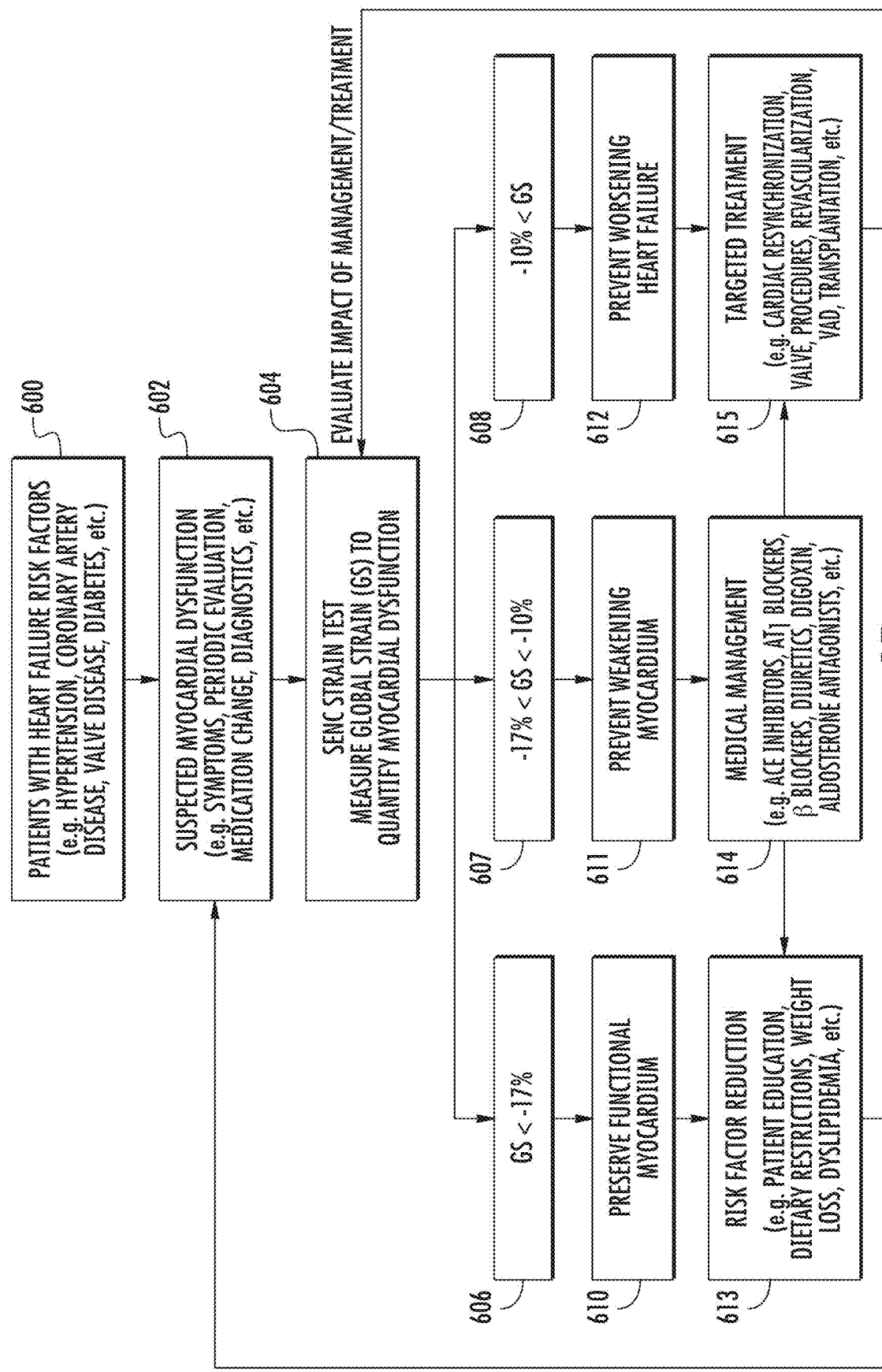
FIG. 17 is a block diagram of an exemplary decision tree to tailor patient management based on quantified SENC strain values for therapeutic decisions that can help to prevent, delay, and/or interrupt heart failure progression according to embodiments of the present invention.

FIG. 17 shows a decision tree to tailor patient management based on quantified SENC strain values and strain mapping to prevent, delay, and/or interrupt heart failure progression.

Patients with heart failure risk factors (e.g. hypertension, coronary artery disease, valve disease, diabetes, etc.) are identified for evaluation (block 600)
Suspected myocardial dysfunction (e.g. symptoms, periodic evaluation, medication change, diagnostics, etc.) (block 602)
SENC Strain Test. Measure Global Strain (GS) to quantify myocardial dysfunction (block 604)
GS<−17% (block 606)
−17%<GS<−10% (block 607)
−10%<GS (block 608)
Preserve functional myocardium (block 610)
Prevent weakening myocardium (block 611)
Prevent worsening heart failure (block 612)
Risk factor reduction (e.g. patient education, dietary restrictions, weight loss, dyslipidemia, etc.) (block 613)
Medical Management (e.g. ACE inhibitors, $AT_1$ blockers, β blockers, diuretics, digoxin, aldosterone antagonists, etc.) (block 614)
Targeted treatment (e.g. cardiac resynchronization, valve, procedures, revascularization, VAD, transplantation, etc.) (block 615).

The targeted treatment and risk factor reduction can be re-evaluated by performing more SENC strain tests after the first SENC strain test (604).

Patients with normal strain, as indicated by global and segmental strain values less than or equal to −17% can be managed to maintain good myocardial function and guide risk factor reduction to prevent myocardial weakening.

Patients with strain between −10% and −17% are characterized by weakened myocardium that is reversible but, left unchecked, will likely progress to heart failure. Patients with reversible myocardial weakening are managed medically or with targeted treatment to improve contractility and address risk factors or underlying conditions that led to reduced myocardial function. By proactively reducing risk factors, prescribing drugs shown to prevent heart failure, and/or referring for interventions to mitigate risk factors or ailments the caused heart dysfunction, reverse remodeling is encouraged before the damage is permanent. For example, a patient with a normal ejection fraction above 50%, normal diastolic function but global strain of −12% (ranging between −10% and −17%) and a history of mitral valve disease with moderate or severe regurgitation may be referred for evaluation of mitral valve repair or replacement to address the underlying condition causing progressive dysfunction before heart failure develops and the damage is permanent.

Repeat or periodic strain tests can evaluate the impact of medical management or targeted treatment on reversible myocardial dysfunction. Prescribed drugs and/or doses can be titrated to optimize improvement in myocardial function under guidance from sequential strain maps. If strain values decrease or remain the same in the abnormal range, changes in prescribed drugs, dosage, or combination drug therapy may be utilized to encourage reverse remodeling and improvement in the underlying condition that caused weakened myocardium or contractility itself.

The impact of targeted treatment (e.g. catheter or surgical intervention) on myocardial function may be quantified with strain maps to determine the relationship between the underlying disease and myocardial weakening or the quality of intervention, and determine subsequent medical management or targeted treatment.

Strain mapping may also be utilized in the perioperative period (e.g. 30 days) after targeted treatment to predict adverse events related to any procedure. For example, pericardial and pleural effusions may cause cardiac dysfunction by increasing the pressure around the heart. Quantification of myocardial dysfunction may provide an early indicator of progressive effects before tamponade occurs, enabling early medical management that avoids the need for emergent draining or adverse sequelae that may result.

Patients with global strain >−10% may have heart failure that will progress to a point where myocardial dysfunction is irreversible. These patients can be managed medically or with targeted treatment to delay or interrupt worsening heart failure and guide initiation of more aggressive interventions before systemic effects ensue and/or complications occur.

Patients undergoing any type of intervention who have pre-existing heart failure, whether or not the ejection fraction is reduced, are at significantly higher risk of complications. Identifying severely diminished myocardial function, even with normal ejection fraction provides an indicator to conservatively manage the patient to prevent adverse events or worsening heart failure. Guiding operative and perioperative management based on pre-operative and peri-operative strain mapping eliminates administering drugs that unknowingly exacerbate myocardial dysfunction. For example, knowing the propensity of the patient to develop heart failure because of pre-existing weakened myocardium encourages and directs utilization of diuretics to prevent the effects of fluid overload, associated with injection of fluid to maintain blood pressure during the index procedure, which can cause or be caused by renal dysfunction.

Patients with worsening heart failure, preceded by progressively and continued weakening myocardial dysfunction, may be candidates of aggressive intervention such as ventricular assist device therapy or heart transplantation. Strain mapping may be used to guide initiation of such treatment modalities before systemic injury results from severely weakened myocardium. Providing a strain metric to justify aggressive intervention standardizes treatment based on quantifiable diagnostic information and minimizes subjective evaluation of the extent of myocardial damage or poor indicators such as ejection fraction obtained by subjective delineation of wall motion.

SENC Applications to Differentiate Systolic from Diastolic Heart Failure

SENC imaging has the ability to measure both systolic dysfunction (i.e. weakening contraction) and diastolic dysfunction (i.e. stiffening myocardium with reduced relaxation).

Figure 18:
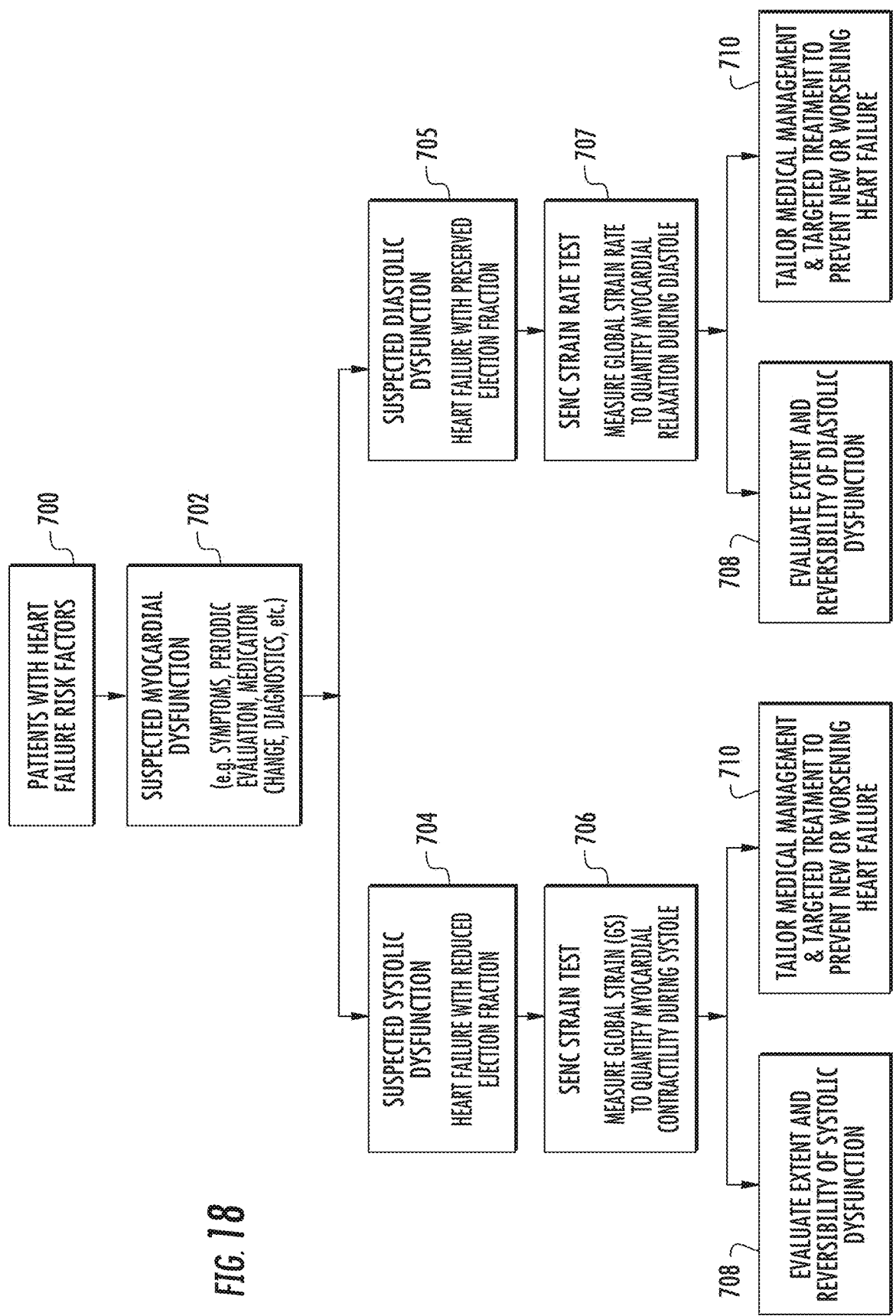
FIG. 18 is a block diagram of an exemplary evaluation protocol describing the ability of SENC imaging to measure both strain and strain rate to quantify the extent and risk of heart failure with reduced ejection fraction indicative of systolic heart failure, and heart failure with preserved ejection fraction indicative of diastolic heart failure according to embodiments of the present invention.

FIG. 18 shows a block diagram describing the use of SENC imaging to measure both strain and strain rate in patients to quantify the extent and risk of heart failure independent of the source of reduced myocardial health. This includes patients at risk of heart failure with reduced ejection fraction indicative of systolic heart failure, and heart failure with preserved ejection fraction indicative of diastolic heart failure.

Patients with heart failure risk factors are identified for evaluation (block 700)

Suspected myocardial dysfunction (e.g. symptoms, periodic evaluation, medication change, diagnostics, etc.) (block 702)

Suspected systolic dysfunction. Heart failure with reduced ejection fraction (block 704)

Suspected diastolic dysfunction. Heart failure with preserved ejection fraction (block 705)

SENC Strain Test. Measure Global Strain (GS) to quantify myocardial contractility during systole) (block 706)

SENC Strain Rate Test. Measure Global Strain Rate to quantify myocardial relaxation during diastole (block 707)

Evaluate extent and reversibility of systolic dysfunction (block 708)

Tailor medical management and targeted treatment to prevent new or worsening heart failure (block 710)

The ability to quantify and compare strain which quantifies myocardial contraction and strain rate which quantifies myocardial relaxation enables delineation of the type of heart failure and guide risk reduction, medical management and/or targeted treatment regimens. By measuring both strain and strain rate and comparing to global values shown to designate normal and abnormal tissue, and further delineate abnormal tissue as reversible or irreversible, the appropriate management strategy can be employed before changes in ejection fraction are identified, at which point either type of heart failure has a poor prognosis.

Embodiments of the Invention

The methods herein may be performed using the subject system, process, or by other means. The methods may all comprise the act of providing a suitable system or process. Such provision may be performed by the end user. In other words, the "providing" (e.g., a SENC imaging system) merely requires the end user obtain, access, approach, position, set-up, activate, power-up or otherwise act to provide the requisite system in the subject method. Methods recited herein may be carried out in any order of the recited events which is logically possible, as well as in the recited order of events. In addition, variations of the invention may be used in imaging other soft tissues that may be subject to deformation such as the aorta (ascending or descending), lung tissue, breast tissue, the liver, gastrointestinal anatomy, or other soft tissue for the identification of cancerous tumors, calcification of segments of the anatomy, or other alteration that causes changes in tissue properties identifiable by evaluating differences in deformation.

Variations in Embodiments

Exemplary variations of the invention are described. Reference of these examples is not limiting. Examples are provided to more broadly illustrate applicable embodiments of the present invention. Changes may be made to the invention described and equivalents may be substituted without departing from the true spirit and scope of the invention. Modifications may be made to adapt a particular situation, algorithm, system component, process, or step to the objectives, spirit or scope of the present invention. All such modifications are intended to be within the scope of the claims made herein. Exemplary aspects of the invention, together with details regarding component selection, algorithm design, and system configuration have been set forth above. As for other details of the present invention, these may be appreciated in connection with the above-referenced patents and publications as well as generally know or appreciated by those with skill in the art.

The same may hold true with respect to method-based aspects of the invention in terms of additional acts as commonly or logically employed. In addition, though the invention has been described in reference to several examples, optionally incorporating various features, the invention is not to be limited to that which is described or indicated as contemplated with respect to each variation of the invention. Various changes may be made to the invention described and equivalents (whether recited herein or not included for the sake of some brevity) may be substituted without departing from the true spirit and scope of the invention. In addition, where a range of values is provided, it is understood that every intervening value, between the upper and lower limit of that range and any other stated or intervening value in that stated range is encompassed within the invention.

Also, it is contemplated that any optional feature of the inventive variations described may be set forth and claimed independently, or in combination with any one or more of the features described herein. Reference to a singular item, includes the possibility that there are plural of the same items present. More specifically, as used herein and in the appended claims, the singular forms "a," "an," "said," and "the" include plural referents unless the specifically stated otherwise. In other words, use of these articles allow for "at least one" of the subject item in the description above as well as the claims below. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in the claims shall allow for the inclusion of any additional element—irrespective of whether a given number of elements are enumerated in the claim, or the addition of a feature could be regarded as transforming the nature of an element set forth in the claims.

That which is claimed:

1. A medical workstation, comprising:
   at least one display; and
   a circuit at least partially onboard or in communication with an MRI Scanner and in communication with the at least one display, the circuit comprising at least one processor configured to:
      obtain a plurality of series of MRI images of long and short axis planes of a heart of a patient, wherein each series of the plurality of series of MRI images is taken over a different single beat of the heart of the patient during an image session associated with a time period for obtaining the plurality of series of MRI images of the long and short axis planes that is five minutes or less of active scan time and with the patient in a bore of the MRI Scanner;
      measure strain of myocardial heart tissue of the heart of the patient based on the plurality of series of MRI images of the heart of the patient;
      generate longitudinal and circumferential heart models with a plurality of adjacent compartments, wherein the compartments are color-coded based on the measured strain;
      obtain a first preliminary series of MRI images of the heart, prior to obtaining the plurality of series of MRI images of long and short axis planes, from transverse, sagittal and coronal planes to generate a pseudo two chamber view of the heart to determine orientation of the heart of the patient in the bore of the MRI Scanner;
      identify a pseudo two-chamber plane or a pseudo four-chamber plane from the obtained first preliminary series of MRI images;
      obtain a second preliminary series of MRI images, prior to obtaining the plurality of series of MRI images of long and short axis planes, from the pseudo two-chamber plane or the pseudo four-chamber plane over a single heartbeat;
      generate a pseudo two-chamber strain encoded movie from the second preliminary series of MRI images of the pseudo two-chamber plane or generate a pseudo four-chamber strain encoded movie from the second preliminary series of MRI images of the pseudo four-chamber plane; then
      identify a pseudo four-chamber plane from the pseudo two chamber strain encoded movie or identify a pseudo two-chamber plane from the pseudo four chamber strain encoded movie;
      identify three short axis imaging planes from the pseudo two chamber strain encoded movie as the three short axis imaging planes for the plurality of series of the MRI images for the strain measurements;
      generate short axis basal (SAB), short axis medial (SAM) and short axis apical (SAA) strain encoded movies from the series of MRI images of the three identified short axis imaging planes; and
      identify three long axis imaging planes from the pseudo two chamber strain encoded movie as the three long axis imaging planes for the plurality of series of MRI images for the strain measurements.

2. The workstation of claim 1, wherein the strain measurements are color-coded in the longitudinal and circumferential heart models to represent five states of heart muscle contractility: hyperkinetic, normokinetic, hypokinetic, akinetic and dyskinetic.

3. The workstation of claim 1, wherein the circuit with the at least one processor is further configured to:
   search the second preliminary series of MRI images from the pseudo two chamber plane and/or the pseudo two chamber strain encoded movie to identify an MRI image with a time with a maximum total intensity signal to identify a close to end systole segment of a cardiac cycle;
   project a line dividing a left ventricle for the identification of the pseudo 4-chamber plane; and
   project three lines dividing the left ventricle for the identification of the three short axis planes.

4. The workstation of claim 3, wherein the second preliminary series of MRI images from the pseudo two chamber plane and/or the pseudo two chamber strain encoded movie used to identify the MRI image with the maximum total intensity signal comprise high tuning raw strain encoded MRI images.

5. The workstation of claim 1, wherein the at least one processor is further configured to evaluate dyssynchrony in heart contraction between chambers of the heart and/or in a single heart chamber of the heart of the patient based on a spatial non-uniformity of strain over a cardiac cycle.

6. The workstation of claim 1, wherein the circuit is further configured to calculate a global strain measurement and compare to predefined global values shown to designate normal and abnormal tissue to thereby delineate abnormal tissue as reversible or irreversible.

7. A medical workstation, comprising:
at least one display; and
a circuit at least partially onboard or in communication with an MRI Scanner and in communication with the at least one display, the circuit comprising at least one processor configured to:
  obtain a first plurality of series of MRI images of long and short axis planes of a heart of a patient, wherein each series of the first plurality of series of MRI images is taken over a different single beat of the heart of the patient during an image session associated with a time period for obtaining the first plurality of series of MRI images of the long and short axis planes that is five minutes or less of active scan time and with the patient in a bore of the MRI Scanner;
  measure strain of myocardial heart tissue of the heart of the patient to generate a first set of strain measurements based on the obtained first plurality of series of MRI images of the heart of the patient;
  generate a first set of longitudinal and circumferential heart models with a plurality of adjacent compartments, wherein the compartments are color-coded based on the measured strain;
  obtain a second plurality of series of MRI images of long and short axis planes of the heart of the patient after a physical or chemically induced stress challenge, wherein each series of the second plurality of series of the MRI images is taken over a different single heartbeat of the heart of the patient during an image session associated with a time period for obtaining the second plurality of series of MRI images of the long and short axis planes that is five minutes or less of active scan time and with the patient in the bore of the MRI Scanner;
  obtain a second set of strain measurements of the myocardial heart tissue of the heart of the patient based on the second plurality of series of MRI images of the heart of the patient; and
  generate:
    a post-challenge set of the longitudinal and circumferential heart models with the plurality of adjacent compartments, wherein the compartments are color-coded based on the second set of strain measurements from the second plurality of series of MRI images; and
    a post-challenge set of the longitudinal and circumferential heart models with the plurality of adjacent compartments, wherein the compartments are color-coded based on a difference between the first and second sets of strain measurements, and
  wherein the circuit is configured to cause the at least one display to concurrently display both of the post-challenge sets of the longitudinal and circumferential heart models with the first set of the longitudinal and circumferential heart models.

8. The workstation of claim 7, wherein the at least one processor is further configured to identify dyssynchrony based on a number between 0 to 1, where "0" represents full dyssynchrony and "1" represents full synchrony, calculated for segments and/or chambers of the heart based on a dispersion of peak shortening over time of the cardiac cycle from the strain measurements obtained at different locations of the heart and different points of time of the cardiac cycle.

9. A medical workstation, comprising:
at least one display; and
a circuit at least partially onboard or in communication with an MRI Scanner and in communication with the at least one display, the circuit comprising at least one processor configured to:
  obtain a first plurality of series of MRI images of long and short axis planes of a heart of a patient, wherein each series of the first plurality of series of MRI images is taken over a different single beat of the heart of the patient during an image session associated with a time period for obtaining the first plurality of series of MRI images of the long and short axis planes that is five minutes or less of active scan time and with the patient in a bore of the MRI Scanner;
  measure strain of myocardial heart tissue of the heart of the patient to generate a first set of strain measurements based on the first plurality of series of MRI images of the heart of the patient;
  generate a first set of longitudinal and circumferential heart models with a plurality of adjacent compartments, wherein the compartments are color-coded based on the measured strain;
  obtain a second plurality of series of MRI images of long and short axis planes of the heart of the patient after a physical or chemically induced stress challenge, wherein each series of the second plurality of series of MRI images is taken over a different single heartbeat of the heart of the patient during an image session associated with a time period for obtaining the second plurality of series of MRI images of the long and short axis planes that is five minutes or less of active scan time and with the patient in the bore of a respective MRI Scanner; and
  measure strain of myocardial heart tissue of the heart of the patient to generate a second set of strain measurements based on the second plurality of series of MRI images of the heart of the patient; and
  generate at least one of:
    a post-challenge set of the longitudinal and circumferential heart models with the plurality of adjacent compartments, wherein the compartments are color-coded based on the second set of strain measurements from the second plurality of series of MRI image slices; or
    a post-challenge set of the longitudinal and circumferential heart models with the plurality of adjacent compartments, wherein the compartments are color-coded based on a difference between the first and second sets of strain measurements, and
  wherein the physical or chemically induced stress challenge is a low stress challenge corresponding to an increase in heart rate of 10-20 beats per minute.

10. A medical workstation, comprising:
at least one display; and
a circuit at least partially onboard or in communication with an MRI Scanner and in communication with the at least one display, the circuit comprising at least one processor configured to:
  obtain a first series of MRI images of a heart of a patient from transverse, sagittal and coronal planes of the heart to determine orientation of the heart of the patient in a bore of the MRI Scanner;
  identify a pseudo two-chamber plane or a pseudo four-chamber plane from the obtained first series of MM images;

obtain a second series of MRI images of the heart from the pseudo two-chamber plane or the pseudo four-chamber plane over a single heartbeat;

generate a pseudo two-chamber strain encoded movie of the heart from the second series of MM images of the pseudo two-chamber plane or generate a pseudo four-chamber strain encoded movie of the heart from the second series of MM images of the pseudo four-chamber plane; then identify a pseudo four-chamber plane from the pseudo two chamber strain encoded movie or identify a pseudo two-chamber plane from the pseudo four chamber strain encoded movie;

identify three short axis imaging planes from the pseudo two chamber strain encoded movie;

identify three long axis imaging planes from the pseudo two chamber strain encoded movie or the pseudo four chamber strain encoded movie;

obtain a third plurality of series of MRI images from the identified long and short axis planes of the heart;

measure strain of myocardial heart tissue of the heart of the patient based on the obtained third plurality of series of MRI images of the heart; and generate longitudinal and circumferential heart models with a plurality of adjacent compartments, wherein the compartments are color-coded based on the measured strain, wherein each series of the third plurality of series of MRI images is taken over a different single heartbeat of the heart of the patient during an image session associated with a time period for obtaining the third plurality of series of MRI images of the long and short axis planes that is five minutes or less of active scan time and with the patient in a bore of the MRI Scanner.

11. The workstation of claim 10, wherein the at least one processor is further configured to:

search the second series of MRI images from the pseudo two chamber plane and/or the pseudo two chamber strain encoded movie to identify an MRI image with a time with a maximum total intensity signal to identify a close to end systole segment of a cardiac cycle; and project a line dividing a left ventricle of the heart in one or more images from the pseudo two chamber strain encoded movie for the identification of the pseudo 4-chamber plane.

12. The workstation of claim 10, wherein the at least one processor is further configured to generate two chamber, three chamber and four chamber strain encoded movies from the obtained third plurality of series of MRI images.

* * * * *

UNITED STATES PATENT AND TRADEMARK OFFICE
CERTIFICATE OF CORRECTION

PATENT NO. : 10,524,687 B2  
APPLICATION NO. : 15/498058  
DATED : January 7, 2020  
INVENTOR(S) : Nael F. Osman Page 1 of 1

It is certified that error appears in the above-identified patent and that said Letters Patent is hereby corrected as shown below:

In the Specification

Column 31, Line 6: Please correct "(e.g. 30 days)" to read -- (e.g. $\leq$ 30 days) --

In the Claims

Column 36, Line 67, Claim 10: Please correct "MM" to read -- MRI --

Column 37, Line 5, Claim 10: Please correct "MM" to read -- MRI --

Column 37, Line 8, Claim 10: Please correct "MM" to read -- MRI --

Signed and Sealed this  
Twelfth Day of May, 2020

Andrei Iancu  
*Director of the United States Patent and Trademark Office*